(12) United States Patent
Ellis et al.

(10) Patent No.: US 7,635,365 B2
(45) Date of Patent: Dec. 22, 2009

(54) BONE PLATES

(76) Inventors: Thomas J. Ellis, 10920 SW. Park Way, Portland, OR (US) 97225; Joel Gillard, 6937 NE. Alameda St., Portland, OR (US) 97213; Steven P. Horst, P.O. Box 456, Dayton, OR (US) 97114

( * ) Notice: Subject to any disclaimer, the term of this patent is extended or adjusted under 35 U.S.C. 154(b) by 808 days.

(21) Appl. No.: 10/927,824

(22) Filed: Aug. 27, 2004

(65) Prior Publication Data
US 2005/0085819 A1  Apr. 21, 2005

Related U.S. Application Data

(60) Provisional application No. 60/498,866, filed on Aug. 28, 2003, provisional application No. 60/548,685, filed on Feb. 26, 2004.

(51) Int. Cl.
*A61B 17/80* (2006.01)

(52) U.S. Cl. ........................................ 606/71

(58) Field of Classification Search ............... 606/61, 606/69–71, 75, 246, 279, 250, 280–299, 606/902–906, 324, 326, 328, 330, 74
See application file for complete search history.

(56) References Cited

U.S. PATENT DOCUMENTS

| | | | |
|---|---|---|---|
| 820,503 A | 5/1906 | Krengel et al. | |
| 869,697 A | 10/1907 | Eilhauer et al. | |
| 1,105,105 A | 7/1914 | Sherman | |
| 1,156,440 A * | 10/1915 | Smith | 606/74 |
| 1,345,425 A | 7/1920 | Wells | |
| 1,789,060 A | 1/1931 | Weisenbach | |
| 1,889,239 A | 11/1932 | Crowley | |
| 1,950,799 A * | 3/1934 | Jones | 606/74 |
| 2,406,832 A | 9/1946 | Hardinge | |
| 2,443,363 A | 6/1948 | Townsend et al. | |
| 2,489,870 A | 11/1949 | Dzus | |
| 2,494,229 A | 1/1950 | Collison | |
| 2,496,126 A | 1/1950 | Haboush | |
| 2,500,370 A | 3/1950 | McKibbin | |
| 2,500,993 A | 3/1950 | Mason | |
| 2,526,959 A | 10/1950 | Lorenzo | |
| 2,579,968 A | 12/1951 | Rush | |
| 2,580,821 A | 1/1952 | Nicola | |
| 2,583,896 A | 1/1952 | Siebrandt | |
| 2,737,835 A | 3/1956 | Herz | |
| 3,025,853 A | 3/1962 | Mason | |

(Continued)

FOREIGN PATENT DOCUMENTS

AU    89750/91    2/1992

(Continued)

OTHER PUBLICATIONS

*Operative stabilization of nonpenetrating chest injuries*, Bryan P. Moore et al., pp. 619-630, 1975.

(Continued)

*Primary Examiner*—Thomas C Barrett
*Assistant Examiner*—James L. Swiger
(74) *Attorney, Agent, or Firm*—Kolisch Hartwell, PC

(57) ABSTRACT

Systems, including methods, apparatus, and kits, for fixing bones, such as rib bones, with bone plates.

26 Claims, 5 Drawing Sheets

U.S. PATENT DOCUMENTS

| | | |
|---|---|---|
| 3,072,423 A | 1/1963 | Charlton |
| 3,171,518 A | 3/1965 | Bergmann |
| 3,244,170 A | 4/1966 | McElvenny |
| 3,346,894 A | 10/1967 | Lemelson |
| 3,357,432 A * | 12/1967 | Sparks ................. 606/151 |
| 3,386,437 A | 6/1968 | Treace |
| 3,488,779 A | 1/1970 | Christensen |
| 3,489,143 A | 1/1970 | Halloran |
| 3,593,709 A | 7/1971 | Halloran |
| 3,604,414 A | 9/1971 | Borges |
| 3,710,789 A * | 1/1973 | Ersek ..................... 606/60 |
| 3,716,050 A | 2/1973 | Johnston |
| 3,726,279 A * | 4/1973 | Barefoot et al. ........... 606/151 |
| 3,741,205 A | 6/1973 | Markolf et al. |
| 3,759,257 A | 9/1973 | Fischer et al. |
| 3,774,244 A | 11/1973 | Walker |
| 3,779,240 A * | 12/1973 | Kondo ..................... 606/69 |
| 3,842,825 A | 10/1974 | Wagner |
| 3,866,458 A | 2/1975 | Wagner |
| 3,900,025 A | 8/1975 | Barnes, Jr. |
| 3,901,064 A | 8/1975 | Jacobsen |
| 3,939,497 A | 2/1976 | Heimke et al. |
| 3,965,720 A | 6/1976 | Goodwin et al. |
| 4,000,525 A | 1/1977 | Klawitter et al. |
| 4,011,863 A | 3/1977 | Zickel |
| 4,055,172 A | 10/1977 | Ender et al. |
| 4,091,806 A | 5/1978 | Aginski |
| 4,119,092 A | 10/1978 | Gil |
| 4,135,507 A | 1/1979 | Harris |
| 4,169,470 A | 10/1979 | Ender et al. |
| 4,187,840 A | 2/1980 | Watanabe |
| 4,187,841 A | 2/1980 | Knutson |
| 4,201,215 A | 5/1980 | Crossett et al. |
| 4,263,904 A | 4/1981 | Judet |
| 4,327,715 A | 5/1982 | Corvisier |
| 4,364,382 A | 12/1982 | Mennen |
| 4,378,607 A | 4/1983 | Wadsworth |
| 4,388,921 A | 6/1983 | Sutter et al. |
| 4,408,601 A | 10/1983 | Wenk |
| RE31,628 E | 7/1984 | Allgower et al. |
| 4,457,307 A | 7/1984 | Stillwell |
| 4,483,335 A | 11/1984 | Tornier |
| 4,484,570 A | 11/1984 | Sutter et al. |
| 4,493,317 A | 1/1985 | Klaue |
| 4,503,847 A | 3/1985 | Mouradian |
| 4,506,662 A | 3/1985 | Anapliotis |
| 4,506,681 A | 3/1985 | Mundell |
| 4,513,744 A | 4/1985 | Klaue |
| 4,565,192 A | 1/1986 | Shapiro |
| 4,565,193 A | 1/1986 | Streli |
| 4,573,458 A | 3/1986 | Lower |
| 4,630,601 A | 12/1986 | Harder et al. |
| 4,651,724 A | 3/1987 | Berentey et al. |
| 4,683,878 A | 8/1987 | Carter |
| 4,703,751 A | 11/1987 | Pohl |
| 4,718,413 A | 1/1988 | Johnson |
| 4,730,608 A | 3/1988 | Schlein |
| 4,733,654 A | 3/1988 | Marino |
| 4,736,737 A | 4/1988 | Fargie et al. |
| 4,743,261 A | 5/1988 | Epinette |
| 4,750,481 A | 6/1988 | Reese |
| 4,757,810 A | 7/1988 | Reese |
| 4,759,350 A | 7/1988 | Dunn et al. |
| 4,760,843 A | 8/1988 | Fischer et al. |
| 4,794,918 A | 1/1989 | Wolter |
| 4,800,874 A | 1/1989 | David et al. |
| 4,823,780 A | 4/1989 | Odensten et al. |
| 4,828,492 A * | 5/1989 | Agnone ................. 433/173 |
| 4,867,144 A | 9/1989 | Karas et al. |
| 4,892,093 A | 1/1990 | Zarnowski et al. |
| 4,893,619 A | 1/1990 | Dale et al. |
| 4,903,691 A | 2/1990 | Heinl |
| 4,905,679 A | 3/1990 | Morgan |
| 4,915,092 A | 4/1990 | Firicá et al. |
| 4,923,471 A | 5/1990 | Morgan |
| 4,926,847 A | 5/1990 | Luckman |
| 4,943,292 A | 7/1990 | Foux |
| 4,955,886 A | 9/1990 | Pawluk |
| 4,957,497 A | 9/1990 | Hoogland et al. |
| 4,963,153 A | 10/1990 | Noesberger et al. |
| 4,964,403 A | 10/1990 | Karas et al. |
| 4,966,599 A | 10/1990 | Pollock |
| 4,973,332 A | 11/1990 | Kummer |
| 4,978,349 A | 12/1990 | Frigg |
| 4,988,350 A | 1/1991 | Herzberg |
| 5,002,544 A | 3/1991 | Klaue et al. |
| 5,006,120 A | 4/1991 | Carter |
| 5,013,314 A | 5/1991 | Firicá et al. |
| 5,013,315 A | 5/1991 | Barrows |
| 5,015,248 A | 5/1991 | Burstein et al. |
| 5,021,056 A | 6/1991 | Hofmann et al. |
| 5,035,697 A | 7/1991 | Frigg |
| 5,041,113 A | 8/1991 | Biedermann et al. |
| 5,042,983 A | 8/1991 | Rayhack |
| 5,049,149 A | 9/1991 | Schmidt |
| 5,053,036 A | 10/1991 | Perren et al. |
| 5,085,660 A | 2/1992 | Lin |
| 5,113,685 A | 5/1992 | Asher et al. |
| 5,116,335 A | 5/1992 | Hannon et al. |
| 5,129,899 A | 7/1992 | Small et al. |
| 5,133,718 A | 7/1992 | Mao |
| 5,135,527 A | 8/1992 | Ender |
| 5,139,497 A | 8/1992 | Tilghman et al. |
| 5,147,361 A | 9/1992 | Ojima et al. |
| 5,151,103 A | 9/1992 | Tepic et al. |
| 5,161,404 A | 11/1992 | Hayes |
| 5,176,685 A | 1/1993 | Rayhack |
| 5,190,544 A | 3/1993 | Chapman et al. |
| 5,190,545 A | 3/1993 | Corsi et al. |
| 5,197,966 A | 3/1993 | Sommerkamp |
| 5,201,736 A | 4/1993 | Strauss |
| 5,201,737 A | 4/1993 | Leibinger et al. |
| 5,234,431 A | 8/1993 | Keller |
| 5,254,119 A | 10/1993 | Schreiber |
| 5,261,908 A | 11/1993 | Campbell, Jr. |
| 5,269,784 A | 12/1993 | Mast |
| 5,290,288 A | 3/1994 | Vignaud et al. |
| 5,304,180 A | 4/1994 | Slocum |
| 5,314,490 A | 5/1994 | Wagner et al. |
| 5,356,410 A | 10/1994 | Pennig |
| 5,364,398 A | 11/1994 | Chapman et al. |
| 5,364,399 A | 11/1994 | Lowery et al. |
| 5,380,327 A | 1/1995 | Eggers et al. |
| 5,413,577 A | 5/1995 | Pollock |
| 5,413,579 A | 5/1995 | Du Toit |
| 5,423,826 A | 6/1995 | Coates et al. |
| 5,443,483 A | 8/1995 | Kirsch |
| 5,443,516 A | 8/1995 | Albrektsson et al. |
| 5,468,242 A | 11/1995 | Reisberg |
| 5,474,553 A | 12/1995 | Baumgart |
| 5,487,741 A | 1/1996 | Maruyama et al. |
| 5,487,743 A | 1/1996 | Laurain et al. |
| 5,522,902 A | 6/1996 | Yuan et al. |
| 5,527,311 A | 6/1996 | Proctor et al. |
| 5,531,745 A | 7/1996 | Ray |
| 5,534,027 A | 7/1996 | Hodorek |
| 5,545,228 A | 8/1996 | Kambin |
| 5,564,302 A | 10/1996 | Watrous |
| 5,571,103 A | 11/1996 | Bailey |
| 5,578,036 A | 11/1996 | Stone et al. |
| 5,586,985 A | 12/1996 | Putnam et al. |
| 5,591,166 A | 1/1997 | Bernhardt et al. |
| 5,601,553 A | 2/1997 | Trebing et al. |
| 5,603,715 A | 2/1997 | Kessler |

| | | | | | | |
|---|---|---|---|---|---|---|
| 5,607,426 A | 3/1997 | Ralph et al. | | 6,129,730 A | 10/2000 | Bono et al. |
| 5,643,261 A | 7/1997 | Schafer et al. | | 6,139,548 A | 10/2000 | Errico |
| 5,643,265 A | 7/1997 | Errico et al. | | 6,152,927 A | 11/2000 | Farris et al. |
| 5,645,599 A * | 7/1997 | Samani .................... 623/17.16 | | 6,159,213 A | 12/2000 | Rogozinski |
| 5,647,872 A | 7/1997 | Gilbert et al. | | 6,179,839 B1 | 1/2001 | Weiss et al. |
| 5,658,283 A | 8/1997 | Huebner | | 6,183,475 B1 | 2/2001 | Lester et al. |
| 5,662,655 A | 9/1997 | Laboureau et al. | | 6,193,721 B1 | 2/2001 | Michelson |
| 5,665,088 A | 9/1997 | Gil et al. | | 6,197,028 B1 | 3/2001 | Ray et al. |
| 5,665,089 A | 9/1997 | Dall et al. | | 6,197,037 B1 | 3/2001 | Hair |
| 5,674,222 A | 10/1997 | Berger et al. | | 6,221,073 B1 | 4/2001 | Weiss et al. |
| 5,676,665 A | 10/1997 | Bryan | | 6,224,602 B1 | 5/2001 | Hayes |
| 5,676,667 A | 10/1997 | Hausman | | 6,228,087 B1 | 5/2001 | Fenaroli et al. |
| 5,681,313 A | 10/1997 | Diez | | 6,235,033 B1 | 5/2001 | Brace et al. |
| 5,702,396 A | 12/1997 | Hoenig et al. | | 6,235,034 B1 | 5/2001 | Bray |
| 5,707,372 A | 1/1998 | Errico et al. | | 6,238,396 B1 | 5/2001 | Lombardo |
| 5,707,373 A | 1/1998 | Sevrain et al. | | 6,258,092 B1 | 7/2001 | Dall |
| 5,709,682 A | 1/1998 | Medoff | | 6,261,291 B1 | 7/2001 | Talaber et al. |
| 5,709,686 A | 1/1998 | Talos et al. | | 6,273,889 B1 | 8/2001 | Richelsoph |
| 5,718,704 A | 2/1998 | Medoff | | 6,280,446 B1 * | 8/2001 | Blackmore .................... 606/74 |
| 5,718,705 A | 2/1998 | Sammarco | | 6,283,969 B1 | 9/2001 | Grusin et al. |
| 5,720,502 A | 2/1998 | Cain | | 6,290,703 B1 | 9/2001 | Ganem |
| 5,722,976 A | 3/1998 | Brown | | 6,302,883 B1 | 10/2001 | Bono |
| 5,722,978 A | 3/1998 | Jenkins, Jr. | | 6,302,884 B1 | 10/2001 | Wellisz et al. |
| 5,728,127 A * | 3/1998 | Asher et al. .................... 606/61 | | 6,302,887 B1 | 10/2001 | Spranza et al. |
| 5,730,743 A | 3/1998 | Kirsch et al. | | 6,306,136 B1 | 10/2001 | Baccelli |
| 5,733,287 A | 3/1998 | Tepic et al. | | 6,312,431 B1 | 11/2001 | Asfora |
| 5,735,853 A | 4/1998 | Olerud | | 6,315,779 B1 | 11/2001 | Morrison et al. |
| 5,741,258 A | 4/1998 | Klaue et al. | | 6,322,562 B1 | 11/2001 | Wolter |
| 5,741,259 A | 4/1998 | Chan | | 6,325,803 B1 | 12/2001 | Schumacher et al. |
| 5,749,872 A | 5/1998 | Kyle et al. | | 6,331,179 B1 | 12/2001 | Freid et al. |
| 5,749,873 A | 5/1998 | Fairley | | 6,336,927 B2 | 1/2002 | Rogozinski |
| 5,752,958 A | 5/1998 | Wellisz | | 6,338,734 B1 | 1/2002 | Burke et al. |
| 5,772,662 A | 6/1998 | Chapman et al. | | 6,342,055 B1 | 1/2002 | Eisermann et al. |
| 5,807,396 A | 9/1998 | Raveh | | 6,342,075 B1 | 1/2002 | MacArthur |
| 5,810,823 A | 9/1998 | Klaue et al. | | 6,355,036 B1 | 3/2002 | Nakajima |
| 5,810,824 A | 9/1998 | Chan | | 6,355,042 B2 | 3/2002 | Winquist |
| 5,814,047 A | 9/1998 | Emilio et al. | | 6,355,401 B1 | 3/2002 | Martin et al. |
| 5,853,413 A | 12/1998 | Carter et al. | | 6,358,250 B1 | 3/2002 | Orbay |
| D404,128 S | 1/1999 | Huebner | | 6,364,881 B1 | 4/2002 | Apgar et al. |
| 5,855,580 A | 1/1999 | Kreidler et al. | | 6,364,882 B1 | 4/2002 | Orbay |
| 5,871,548 A | 2/1999 | Sanders et al. | | 6,364,883 B1 | 4/2002 | Santilli |
| 5,879,389 A | 3/1999 | Koshino | | 6,379,354 B1 | 4/2002 | Rogozinski |
| 5,902,304 A | 5/1999 | Walker et al. | | 6,379,359 B1 | 4/2002 | Dahners |
| 5,904,683 A | 5/1999 | Pohndorf et al. | | 6,379,364 B1 | 4/2002 | Brace et al. |
| 5,916,216 A | 6/1999 | DeSatnick et al. | | 6,402,756 B1 | 6/2002 | Ralph et al. |
| 5,919,195 A | 7/1999 | Wilson et al. | | 6,413,259 B1 | 7/2002 | Lyons et al. |
| 5,928,234 A | 7/1999 | Manspeizer | | 6,428,542 B1 | 8/2002 | Michelson |
| 5,931,839 A | 8/1999 | Medoff | | 6,436,103 B1 | 8/2002 | Suddaby |
| 5,938,664 A | 8/1999 | Winquist et al. | | 6,440,135 B2 | 8/2002 | Orbay et al. |
| 5,941,878 A | 8/1999 | Medoff | | 6,454,769 B2 | 9/2002 | Wagner et al. |
| 5,951,557 A | 9/1999 | Luter | | 6,454,770 B1 | 9/2002 | Klaue |
| 5,954,722 A | 9/1999 | Bono | | 6,458,133 B1 | 10/2002 | Lin |
| 5,964,763 A | 10/1999 | Incavo et al. | | 6,503,250 B2 | 1/2003 | Paul |
| 5,968,046 A | 10/1999 | Castleman | | 6,508,819 B1 | 1/2003 | Orbay |
| 5,968,047 A | 10/1999 | Reed | | 6,514,274 B1 | 2/2003 | Boucher et al. |
| 5,973,223 A | 10/1999 | Tellman et al. | | 6,520,965 B2 | 2/2003 | Chervitz et al. |
| 6,001,099 A | 12/1999 | Huebner | | 6,527,775 B1 | 3/2003 | Warburton |
| 6,004,323 A | 12/1999 | Park et al. | | 6,533,789 B1 | 3/2003 | Hall, IV et al. |
| 6,004,353 A | 12/1999 | Masini | | 6,547,790 B2 | 4/2003 | Harkey et al. |
| 6,007,535 A | 12/1999 | Rayhack et al. | | 6,565,570 B2 | 5/2003 | Sterett et al. |
| 6,007,538 A * | 12/1999 | Levin ......................... 606/71 | | 6,572,620 B1 | 6/2003 | Schon et al. |
| 6,022,350 A | 2/2000 | Ganem | | 6,592,578 B2 | 7/2003 | Henniges et al. |
| 6,027,504 A | 2/2000 | McGuire | | 6,595,993 B2 | 7/2003 | Donno et al. |
| 6,053,915 A | 4/2000 | Bruchmann | | 6,602,255 B1 | 8/2003 | Campbell et al. |
| 6,077,266 A | 6/2000 | Medoff | | 6,623,486 B1 | 9/2003 | Weaver et al. |
| 6,077,271 A | 6/2000 | Huebner et al. | | 6,623,487 B1 | 9/2003 | Goshert |
| 6,093,188 A | 7/2000 | Murray | | 6,682,531 B2 | 1/2004 | Winquist et al. |
| 6,096,040 A | 8/2000 | Esser | | 6,682,533 B1 | 1/2004 | Dinsdale et al. |
| 6,113,603 A | 9/2000 | Medoff | | 6,689,139 B2 | 2/2004 | Horn |
| 6,117,139 A | 9/2000 | Shino | | 6,695,846 B2 | 2/2004 | Richelsoph et al. |
| 6,117,160 A | 9/2000 | Bonutti | | 6,706,046 B2 | 3/2004 | Orbay et al. |
| 6,123,709 A | 9/2000 | Jones | | 6,712,820 B2 | 3/2004 | Orbay |
| 6,129,728 A | 10/2000 | Schumacher et al. | | 6,719,759 B2 | 4/2004 | Wagner et al. |

| | | |
|---|---|---|
| 6,730,090 B2 | 5/2004 | Orbay et al. |
| 6,730,091 B1 | 5/2004 | Pfefferle et al. |
| 6,736,819 B2 | 5/2004 | Tipirneni |
| 6,767,351 B2 | 7/2004 | Orbay et al. |
| 6,793,658 B2 | 9/2004 | LeHuec et al. |
| 6,821,278 B2 | 11/2004 | Frigg et al. |
| 6,858,031 B2 | 2/2005 | Morrison et al. |
| 6,863,694 B1 | 3/2005 | Boyce et al. |
| 6,866,665 B2 | 3/2005 | Orbay |
| 6,893,444 B2 | 5/2005 | Orbay |
| 6,955,677 B2 | 10/2005 | Dahners |
| 2001/0011172 A1 | 8/2001 | Orbay et al. |
| 2002/0004660 A1 | 1/2002 | Henniges et al. |
| 2002/0032446 A1 | 3/2002 | Orbay |
| 2002/0055741 A1 | 5/2002 | Schlapfer et al. |
| 2002/0128654 A1 | 9/2002 | Steger et al. |
| 2002/0143336 A1 | 10/2002 | Hearn |
| 2002/0143337 A1 | 10/2002 | Orbay et al. |
| 2002/0143338 A1 | 10/2002 | Orbay et al. |
| 2002/0147453 A1 | 10/2002 | Gambale |
| 2002/0151899 A1 | 10/2002 | Bailey et al. |
| 2002/0156474 A1 | 10/2002 | Wack et al. |
| 2002/0183752 A1 | 12/2002 | Steiner et al. |
| 2003/0040748 A1 | 2/2003 | Aikins et al. |
| 2003/0055429 A1 | 3/2003 | Ip et al. |
| 2003/0105461 A1 | 6/2003 | Putnam |
| 2003/0149434 A1 | 8/2003 | Paul |
| 2003/0153918 A1 | 8/2003 | Putnam et al. |
| 2003/0233093 A1 | 12/2003 | Moles et al. |
| 2004/0102775 A1 | 5/2004 | Huebner |
| 2004/0102776 A1 | 5/2004 | Huebner |
| 2004/0102777 A1 | 5/2004 | Huebner |
| 2004/0102778 A1 | 5/2004 | Huebner |
| 2004/0116930 A1 | 6/2004 | O'Driscoll et al. |
| 2004/0127901 A1 | 7/2004 | Huebner et al. |
| 2004/0127903 A1 | 7/2004 | Schlapfer et al. |
| 2004/0127904 A1 | 7/2004 | Konieczynki et al. |
| 2004/0153073 A1 | 8/2004 | Orbay |
| 2004/0186472 A1 | 9/2004 | Lewis et al. |
| 2004/0193164 A1 | 9/2004 | Orbay |
| 2004/0193165 A1 | 9/2004 | Orbay |
| 2004/0220566 A1 | 11/2004 | Bray |
| 2004/0260291 A1 | 12/2004 | Jensen |
| 2004/0260292 A1 | 12/2004 | Orbay et al. |
| 2004/0260293 A1 | 12/2004 | Orbay et al. |
| 2004/0260294 A1 | 12/2004 | Orbay et al. |
| 2004/0260295 A1 | 12/2004 | Orbay et al. |
| 2005/0015089 A1 | 1/2005 | Young et al. |
| 2005/0049593 A1 | 3/2005 | Duong et al. |
| 2005/0065520 A1 | 3/2005 | Orbay |
| 2005/0065522 A1 | 3/2005 | Orbay |
| 2005/0065523 A1 | 3/2005 | Orbay |
| 2005/0065524 A1 | 3/2005 | Orbay |
| 2005/0065528 A1 | 3/2005 | Orbay |
| 2005/0070902 A1 | 3/2005 | Medoff |
| 2005/0085818 A1 | 4/2005 | Huebner |
| 2005/0131413 A1 | 6/2005 | O'Driscoll et al. |
| 2005/0159747 A1 | 7/2005 | Orbay |
| 2005/0165395 A1 | 7/2005 | Orbay et al. |
| 2005/0165400 A1 | 7/2005 | Fernandez |
| 2005/0171544 A1 | 8/2005 | Falkner |
| 2005/0182405 A1 | 8/2005 | Orbay et al. |
| 2005/0182406 A1 | 8/2005 | Orbay et al. |
| 2005/0187551 A1 | 8/2005 | Orbay et al. |
| 2005/0192578 A1 | 9/2005 | Horst |
| 2005/0234458 A1 | 10/2005 | Huebner |
| 2006/0085000 A1 | 4/2006 | Mohr et al. |
| 2006/0100623 A1 | 5/2006 | Pennig |
| 2007/0043367 A1 | 2/2007 | Lawrie |
| 2007/0043368 A1 | 2/2007 | Lawrie et al. |
| 2007/0083202 A1 | 4/2007 | Eli Running et al. |
| 2007/0185493 A1 | 8/2007 | Feibel et al. |

FOREIGN PATENT DOCUMENTS

| | | |
|---|---|---|
| CH | 576249 | 6/1976 |
| CH | 611 147 | 5/1979 |
| DE | 2515430 | 11/1975 |
| DE | 3 808 937 | 10/1989 |
| DE | 4201531 | 7/1993 |
| DE | 4343117 | 6/1995 |
| EP | 0 053 999 | 6/1982 |
| EP | 0029752 | 4/1983 |
| EP | 0094039 A1 | 5/1983 |
| EP | 0 179 695 | 4/1986 |
| EP | 0 410 309 | 1/1991 |
| EP | 0415837 A2 | 3/1991 |
| EP | 0471418 A1 | 2/1992 |
| EP | 0362049 B1 | 5/1992 |
| EP | 0561295 B1 | 5/1996 |
| EP | 1 250 892 A2 | 9/2003 |
| EP | 1 250 892 A3 | 9/2003 |
| FR | 742.618 | 3/1933 |
| FR | 2 211 851 A | 7/1974 |
| FR | 2 254 298 | 7/1975 |
| FR | 2367479 | 5/1978 |
| FR | 2405705 | 5/1979 |
| FR | 2405706 | 5/1979 |
| FR | 2406429 | 5/1979 |
| FR | 2 416 683 A | 9/1979 |
| FR | 2472373 | 7/1981 |
| FR | 2674118 | 9/1992 |
| GB | 224598 | 1/1992 |
| GB | 2 331 244 A9 | 5/1999 |
| GB | 2 435 429 A | 8/2007 |
| SU | 610518 | 6/1978 |
| SU | 718097 | 2/1980 |
| SU | 862937 | 9/1981 |
| SU | 874044 | 10/1981 |
| SU | 897233 | 1/1982 |
| SU | 921553 | 4/1982 |
| SU | 1049054 | 10/1983 |
| SU | 1130332 | 12/1984 |
| SU | 1192806 | 11/1985 |
| SU | 1223901 | 4/1986 |
| SU | 1225556 | 4/1986 |
| SU | 1544406 | 2/1990 |
| SU | 1630804 | 2/1991 |
| SU | 1644932 | 4/1991 |
| SU | 1683724 | 10/1991 |
| SU | 1711859 A | 2/1992 |
| SU | 1734715 A1 | 5/1992 |
| WO | WO82/01645 | 5/1982 |
| WO | WO87/02572 | 5/1987 |
| WO | WO88/03781 | 6/1988 |
| WO | 9505782 A | 3/1995 |
| WO | WO96/29948 | 10/1996 |
| WO | WO 97/47251 | 12/1997 |
| WO | WO 9922089 | 5/1999 |
| WO | WO01/21083 A1 | 3/2001 |
| WO | WO01/62136 A3 | 8/2001 |
| WO | WO 03/105712 A2 | 12/2003 |
| WO | 2007092813 A2 | 8/2007 |

OTHER PUBLICATIONS

*Surgical stabilization of traumatic flail chest*, F. Twrazona et al., pp. 521-527, 1975.
*Operative stabilization for flail chest after blunt trauma*, Arthur N. Thomas et al., *The Journal of Thoracic and Cardiovascular Surgery*, vol. 75, No. 6, pp. 793-801, Jun. 1978.
*Chest Wall Injuries*, Trunkey DD, Cerviothoracic Trauma, vol. 3. pp. 129-149, 1986.

*Rib Fracture Healing after Osteosynthesis with Wire Mesh Titanium and Screws: A Histological Study in Sheep*, Klein et al., pp. 347-354, 1989.
*Open Fixation of Flail Chest After Blunt Trauma*, George B. Haasler, MD, *The Society of Thoracic Surgeons*, pp. 993-995, 1990.
*Strut Fixation of an Extensive Flail Chest*, Rodney J. Laudreneau, MD et al., *The Society of Thoracic Surgeons*, pp. 473-475, 1991.
*Operative Chest Wall Stabilization in Flail Chest—Outcomes of Patients With or Without Pulmonary Contusion*, Gregor Voggenreiter, MD et al., *American College of Surgeons*, pp. 130-138, 1998.
*Use of 3.5mm Acetabular Reconstruction Plates for Interal Fixation of Flail Chest Injuries*, J. Rodrigo Oyarzun et al., *Section of Cardiothoracic Surgery*, pp. 1471-1474, 1998.
*Bioabsorable Poly-L-Lactide Costal Coaptation Pins and Their Clinical Application in Thoroacotomy*, Akitoshi Tatsumi et al., *Original Articles: General Thoracic*. pp. 765-768, 1999.
*Painful Nonunion of Multiple Rib Fractures Managed by Operative Stabilization*, Robert Cacchione, MD et al., *The Journal of Trauma, Injury, Infection and Critical Care*, vol. 48, No. 2, pp. 319-321, 2000.
*Internal Fixation in Osteoporotic Bone, An*, Y.H., pp. 83, 2002.
*Absorable Plates for Rib Fracture Repair: Preliminary Experience*, John C. Mayberry, *Journal of Trauma Injury, Infection and Critical Care*. vol. 55, No. 5, pp. 835-839, Nov. 2003.
*Clinically Oriented Anatomy*, Keith Moore et al., Fourth Edition, pp. 70-71, 2004.
Operative Chest Wall Fixation with Osteosynthesis Plates, Christine Engel et al., *The Journal of Trauma, Injury, Infection and Critical Care*, vol. 58, No. 1, pp. 181-186, 2005.
*Biomechanics Laboratory*, Legacy Biomechanics Laboratory, available at www.biomechresearch.org/sling.html, Jan. 2006.
*Resorable Plates* from Osteomed, available at www.osteomedcorp.com/images/library/resorbfixation.gif, Feb. 2006.
*Rib Plate*, from Sanatmetal Catalog, available at www.sanatmetal.hu/catalog/pict/1_5_89a_1.jpg, Feb. 2006.
*Biomechanical Evaluation of the Schuhli Nut*, Kolodziej, et al., *Clinical Orthopaedics and Related Research*, vol. 347, pp. 79-85, Feb. 1998.
Internal Fixation in Osteoporotic Bone, An, Y.H., p. 83, 2002.
*Zespol Bone Screws*, in *Mikromed—Catalogue 2004* (Nov. 2004), available at http://www.mikromed.pl/katalog/Main/main_eng.htm and http://www.mikromed.pl/katalog/zespol_eng/wkrety.htm.
*Zespol Bone Plates*, in *Mikromed—Catalogue 2004* (Nov. 2004), available at http://www.mikromed.pl/katalog/Main/main_eng.htm and http://www.mikromed.pl/katalog/zespol_eng/plytki.htm.
SmartLock Locking Screw Technology, advertisement, *The Journal of Hand Surgery*, vol. 30A, No. 1, Jan. 2005.
European Patent Office, European Patent Application No. EP 04 78 2685; search date: Oct. 10, 2008.
McBride S.M.O. Stainless Steel Bone Plates brochure, DePuy, Inc., 1943.
Bone Plates brochure, Vitallium, Mar. 1948.
Dupont Distal Humeral Plates brochure, Howmedica Inc., 1990.
The Arnett-TMP* Titanium Miniplating System brochure, Techmedica, Inc., 1989.
Techmedica Bioengineers Keep Tabs on Your Needs brochure, Techmedica, Inc., 1991.
*A Comparison of Unicortical and Bicortical End Screw Attachment of Fracture Fixation Plates*, Beaupre et al., *Journal of Orthopaedic Trauma*, vol. 6, No. 3, pp. 294-300, 1992.
Ace 4.5/5.0 mm Titanium Cannulated Screw and Reconstruction Plate System surgical technique brochure, Ace Medical Company, 1992.
Ace 4.5/5.0 mm Titanium Cannulated Screw and Reconstruction Plate System simplified fracture fixation brochure, Ace Medical Company, 1992.
Ace Titanium 3.5/4.0 mm Screw and Plate System with the Ace 3.5 mm Universal Ribbon CT/MRI compatible fixation brochure, Ace Medical Company, 1992.
*Treatment of Three- and Four-Part Fractures of the Proximal Humerus with a Modified Cloverleaf Plate*, Esser, *Journal of Orthopaedic Trauma*, vol. 8, No. 1, pp. 15-22, 1994.
Ace Symmetry Titanium Upper Extremity Plates surgical technique brochure, Ace Medical Company, 1996.

The Ace Symmetry Titanium Upper Extremity Plates new product release brochure, Ace Medical Company, 1996.
Small Titanium Plates overview page, Synthes, p. 2a-33, Mar. 1997.
Congruent Distal Radius Plate System description, Acumed, Inc., Mar. 4, 1998.
*Salvage of Tibial Pilon Fractures Using Fusion of the Ankle with a 90° Cannulated Blade Plate: A Preliminary Report*, Morgan et al., *Foot & Ankle International*, vol. 20, No. 6, pp. 375-378, Jun. 1999.
*Scaphoid Protocols Using the Acutrak® Bone Screw System* brochure, Toby, published by Acumed, Inc., Dec. 7, 1999.
Single Unit Osteosynthesis brochure, Surfix Technologies, Sep. 2000.
Supracondylar Cable Plate brochure, Biomet Orthopedics, Inc., 2000.
*Principle-Based Internal Fixation of Distal Humerus Fractures*, Sanchez-Sotelo et al., *Techniques in Hand & Upper Extremity Surgery*, vol. 5, No. 4, pp. 179-187, Dec. 2001.
Congruent Plate System—The Mayo Clinic Congruent Elbow Plates brochure, Acumed, Inc., May 7, 2002.
Modular Hand System brochure, Acumed, Inc., Aug. 2002.
Modular Hand System brochure, Acumed, Inc., Sep. 2002.
Periarticular Plating System brochure, Zimmer, Inc., 2002.
Jplate Diaphysis Plates for Japanese brochure, Mizuho Co., Ltd., 2002.
*An Axially Mobile Plate for Fracture Fixation*, Abel et al., *Internal Fixation in Osteoporotic Bone*, pp. 279-283, 2002.
*The Use of Interlocked 'Customised' Blade Plates in the Treatment of Metaphyseal Fractures in Patients with Poor Bone Stock*, Palmer et al., *Injury, Int. J. Care Injured*, vol. 31, pp. 187-191, 2002.
3.5 mm LCP™ Proximal Humerus Plate technique guide, Synthes (USA), 2002.
Titanium Wire Plate Osteosynthesis System According to Dr. Gahr internet printout, Erothitan Titanimplantate AG, print date Feb. 6, 2003.
Bilder internet printout, Martin GmbH & Co. KG, print date Sep. 5, 2003.
International Search Report for PCT Patent Application Serial No. PCT/US03/22904, Dec. 4, 2003.
*The Use of a Locking Custom Contoured Blade Plate for Peri-Articular Nonunions*, Harvey et al., *Injury, Int. J. Care Injured*, vol. 34, pp. 111-116, 2003.
*Salvage of Distal Tibia Metaphyseal Nonunions With the 90° Cannulated Blade Plate*, Chin et al., *Clinical Orthopaedics and Related Research*, No. 409, pp. 241-249, 2003.
Rib Securing Clamped Plate internet printout, Sanatmetal, print date Sep. 22, 2004.
*Biological Plating: A New Concept to Foster Bone Healing*, Synthes (USA), 1991.
*Treatment by Plates of Anteriorly Displaced Distal Radial Fractures*, Ducloyer, *Fractures of the Distal Radius*, pp. 148-152, 1995.
*Management of Comminuted Distal Radial Fractures*, Jupiter et al., *Fractures of the Distal Radius*, pp. 167-183, 1995.
*Open Reduction of Intra-Articular Fractures of the Distal Radius*, Amadio, *Fractures of the Distal Radius*, pp. 193-202, 1995.
May Anatomical bone Plates: Plates, Bone Screws and Instruments brochure, pp. 3-4 and 10-15, Waldemar Link GmbH & Co., 1995.
Forte Distal Radial Plate System brochure, Zimmer, Inc., 1995.
*Design and Biomechanics of a Plate for the Distal Radius*, Gesensway et al., *Journal of Hand Surgery*, vol. 20, No. 6, pp. 1021-1027, 1995 (abstract only provided).
*Fractures of the Distal Radius: A Practical Approach to Management*, Fernandez et al., pp. 103-188, 1996.
Titanium Distal Radius Instrument and Implant Set standard contents description pages, Synthes, Mar. 1997.
*Prospective Multicenter Trial of a Plate for Dorsal Fixation of Distal Radius Fractures*, Ring et al., *The Journal of Hand Surgery*, vol. 22A, No. 5, pp. 777-784, Sep. 1997.
*Treatment of Displaced Intra-Articular Fractures of the Distal End of the Radius With Plates*, Fitoussi et al., *The Journal of Bone and Joint Surgery*, vol. 79, No. 9, pp. 1303-1312, 1997 (abstract only provided).
The Titanium Distal Radius Plate, technique guide, Synthes (USA), 1997.

TriMed Wrist Fixation System brochure, TriMed, Inc., 1997.
SCS/D Distal Radius Plate System brochure, Avanta Orthopaedics, 1997.
*Intra-Articular Fractures of the Distal Aspect of the Radius*, Trumble et al., *Journal of Bone and Joint Surgery*, vol. 80A, No. 4, pp. 582-600, Apr. 1998.
*Complications of the AO/ASIF Titanium Distal Radius Plate System (πPlate) in Internal Fixation of the Distal Radius: A Brief Report*, Kambouroglou et al., *Journal of Hand Surgery*, vol. 23A, No. 4, pp. 737-741, Jul. 1998.
SCS/V Distal Radius Plate Volar brochure, Avanta Orthopaedics, 1998.
*Delayed Rupture of the Flexor Pollicies Longus Tendon After Inappropriate Placement of the π Plate on the Volar Surface of the Distal Radius*, Nunley et al., *Journal of Hand Surgery*, vol. 24, No. 6, pp. 1279-1280, Nov. 1999.
TiMAX Pe.R.I. Small Fragment Upper Extremity description pages, DePuy ACE Medical Company, 1999.
The Distal Radius Plate Instrument and Implant Set technique guide, Synthes (USA), 1999.
*Outcome Following Nonoperative Treatment of Displaced Distal Radius Fractures in Low-Demand Patients Older Than 60 Years*, Young, *Journal of Hand Surgery*, vol. 25A, No. 1, pp. 19-28, Jan. 2000.
*Comparison of Three Different Plating Techniques for the Dorsum of the Distal Radius: A Biomechanical Study*, Peine et al., *Journal of Hand Surgery*, vol. 25A, No. 1, pp. 29-33, Jan. 2000.
*Distal Radial Metaphyseal Forces in an Extrinsic Grip Model: Implications for Postfracture Rehabilitation*, Putnam et al., *Journal of Hand Surgery*, vol. 25A, No. 3, pp. 469-475, May 2000.
TriMed Wrist Fixation System internet description pages, TriMed, Inc., 2001.
Titanium Distal Radius Plates description page, Synthes (USA), 2001.
Locon-T Distal Radius Plating System case study and surgical method, Wright Medical Technology, Inc., 2001.
*Open Reduction and Internal Fixation of Unstable Distal Radius Fractures: Results Using the Trimed Fixation System*, Konrath et al., *Journal of Orthopaedic Trauma*, vol. 16, No. 8, pp. 578-585, 2002.
Locon-T Distal Radius Plating System brochure, Wright Medical Technology, Inc., 2002.

*Distal Radius Fracture*, Tornetta, *Journal of Orthopaedic Trauma*, vol. 16, No. 8, pp. 608-611, 2002.
*Comparison of Different Distal Radius Dorsal and Volar Fracture Fixation Plates: A Biomechanical Study*, Osada et al., *Journal of Hand Surgery*, vol. 28A, No. 1, pp. 94-104, Jan. 2003.
*Tendon Function and Morphology Related to Material and Design of Plates For Distal Radius Fracture Fixation: Canine Forelimb Model*, Turner et al., Orthopaedic Research Society, Feb. 2003.
*Fractures of the Distal Aspect of the Radius: Changes in Treatment Over the Past Two Decades*, Simic, *Journal of Bone and Joint Surgery*, vol. 85-A, No. 3, pp. 552-564, Mar. 2003.
*Palmar Plate Fixation of AO Type C2 Fracture of Distal Radius Using a Locking Compression Plate—A Biomechanical Study in a Cadaveric Model*, Leung et al., *Journal of Hand Surgery*, vol. 28B, No. 3, pp. 263-266, Jun. 2003.
*Functional Outcome and Complications Following Two Types of Dorsal Plating for Unstable Fractures of the Distal Part of the Radius*, Rozental et al., *Journal of Bone and Joint Surgery*, vol. 85, No. 10, pp. 1956-1960, 2003 (abstract only provided).
*Fixation of Unstable Fractures of the Volar Rim of the Distal Radius with a Volar Buttress Pin®*, Hooker et al., 2003.
*Results of Palmar Plating of the Lunate Facet Combined with External Fixation for the Treatment of High Energy Compression Fractures of the Distal Radius*, Ruch et al., *J. Orthop. Trauma*, Vo. 18, No. 1, pp. 28-33, Jan. 2004.
Synthes Volar Distal Radius Locking Plate internet description page, Orthocopia, LLC, 2004.
U.K. Intellectual Property Office, Patents Act 1977: Combined Search and Examination Report under Sections 17 and 18(3), United Kingdom Patent Application No. GB0810872.2; search date: Sep. 4, 2008.
Lardinois, D. et al. *Pulmonary Function Testing After Operative Stabilisation of the Chest Wall for Flail Chest. European Journal of Cardio-thoracic Surgery* (2001) 20:496-501.
Ng, A. et al. *Operative Stabilisation of Painful Non-united Multiple Rib Fractures. Injury* (2001) 32:637-639.
Slater, M. et al. *Operative Stabilization of Flail Chest Six Years After Injury, Annals of Thoracic Surgery* (2001) August:600-601.
Tanaka, H. et al. *Surgical Stabilization or Internal Pneumatic Stabilization? A Prospective Randomized Study of Management of Severe Flail Chest Patients. Journal of Trauma* (2002) 52:727-732.

* cited by examiner

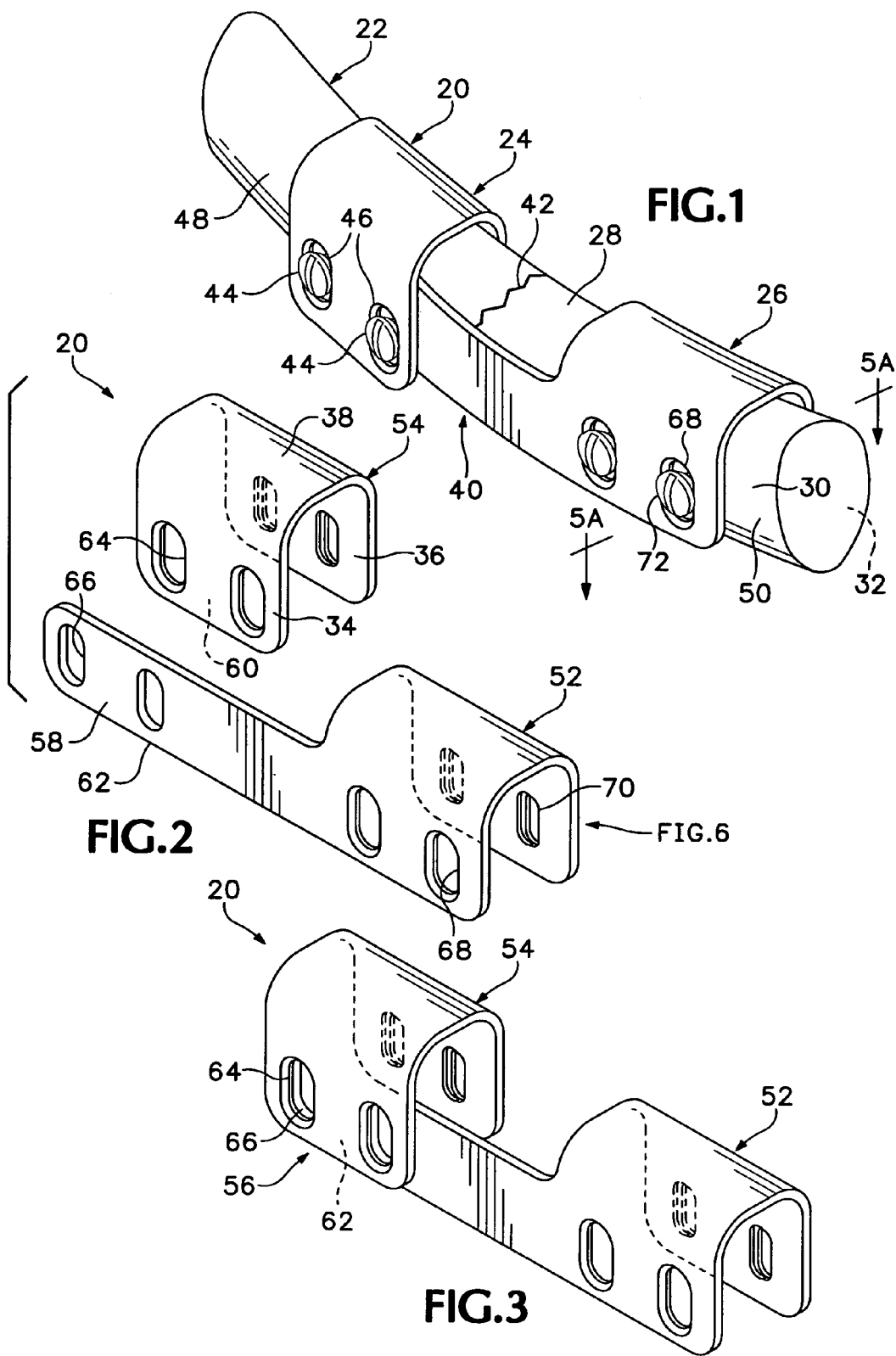

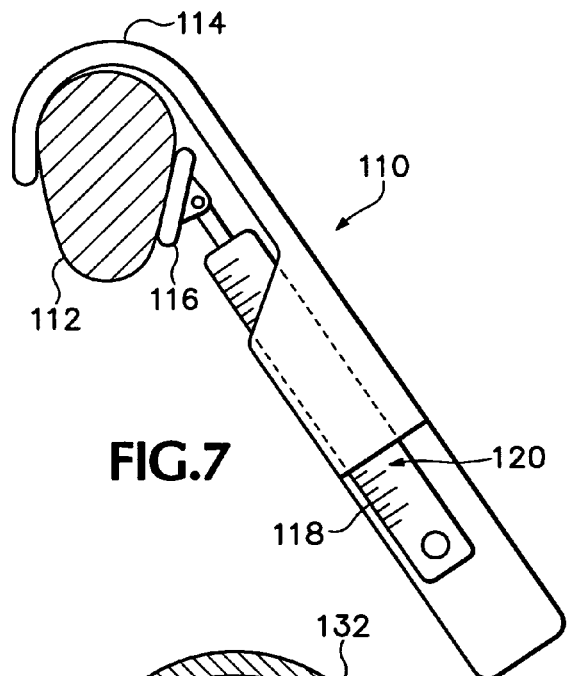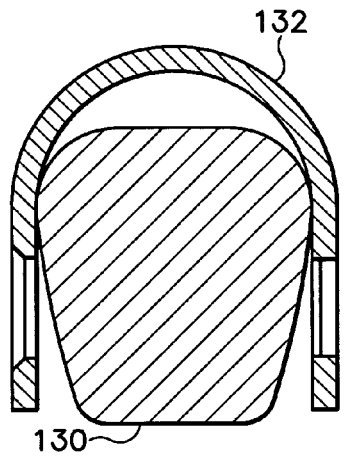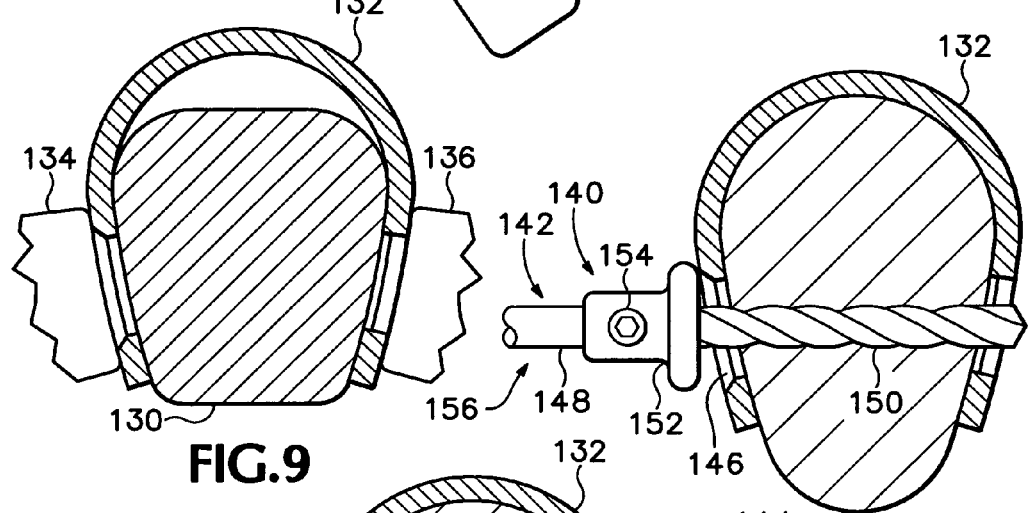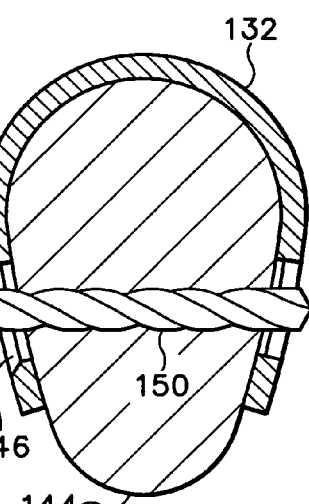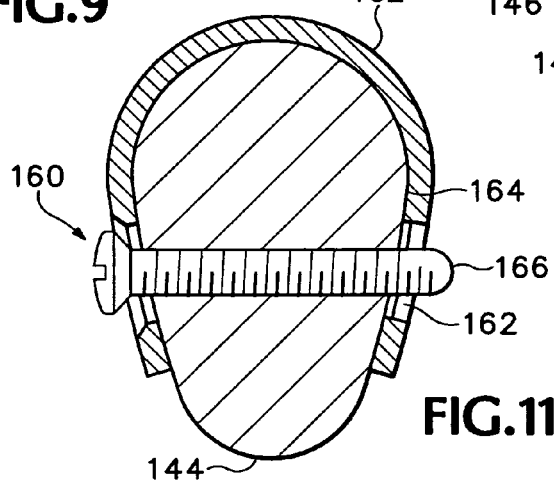

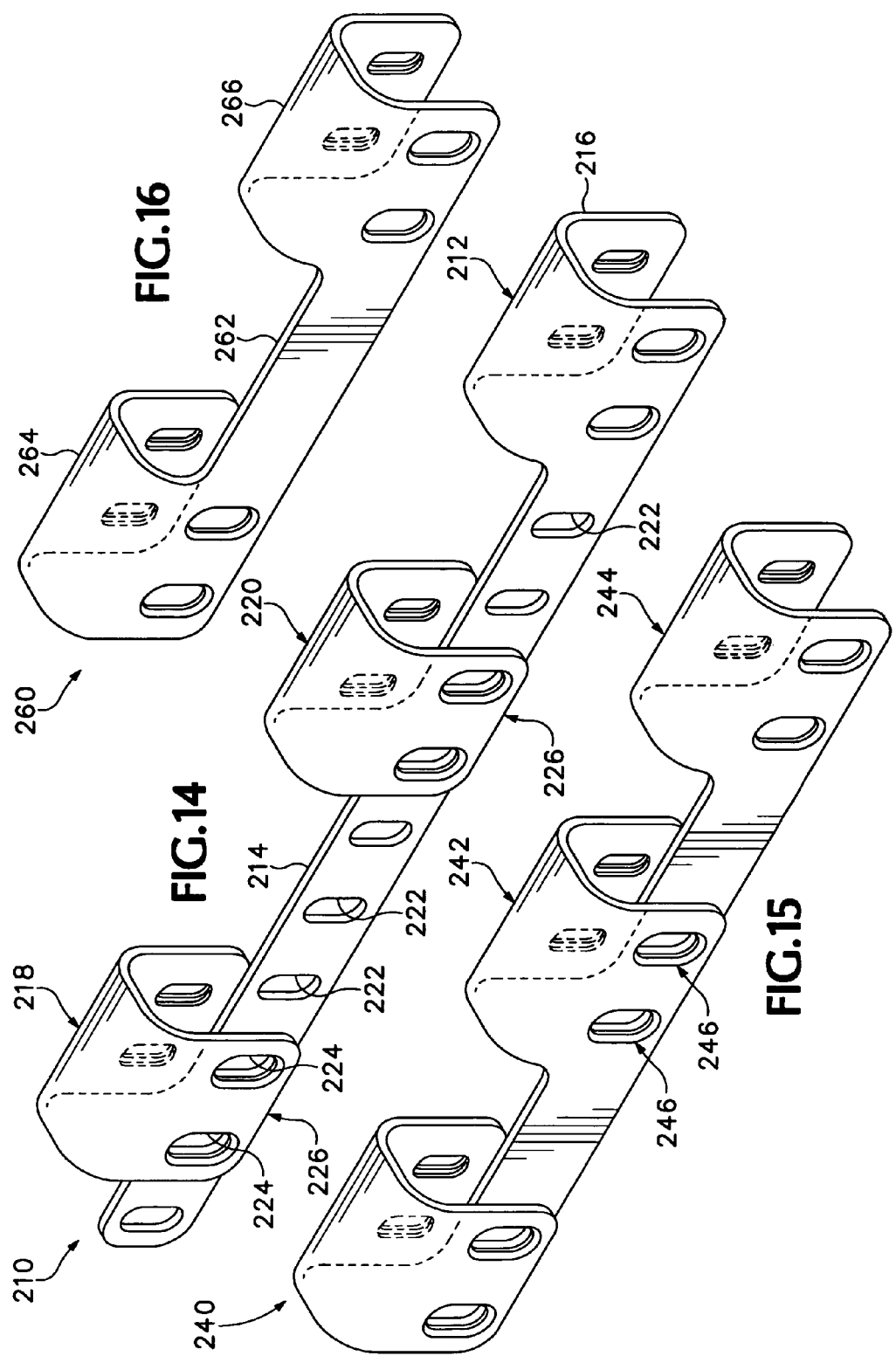

BONE PLATES

CROSS-REFERENCE TO PRIORITY APPLICATION

This application is based upon and claims the benefit under 35 U.S.C. § 119(e) of the following U.S. provisional patent applications: Ser. No. 60/498,866, filed Aug. 28, 2003; and Ser. No. 60/548,685, filed Feb. 26, 2004. These applications are incorporated herein by reference in their entirety for all purposes.

BACKGROUND

The human skeleton is composed of 206 individual bones that perform a variety of important functions, including support, movement, protection, storage of minerals, and formation of blood cells. These bones can be grouped into two categories, the axial skeleton and the appendicular skeleton. The axial skeleton consists of 80 bones that make up the body's center of gravity, and the appendicular skeleton consists of 126 bones that make up the body's appendages. The axial skeleton includes the skull, vertebral column, ribs, and sternum, among others, and the appendicular skeleton includes the long bones of the upper and lower limbs, and the clavicles and other bones that attach these long bones to the axial skeleton, among others.

To ensure that the skeleton retains its ability to perform its important functions, and to reduce pain and disfigurement, fractured bones should be repaired promptly and properly. Typically, fractured bones are treated using fixation devices, which reinforce the fractured bones and keep them aligned during healing. Fixation devices may take a variety of forms, including casts for external fixation and bone plates for internal fixation, among others. Casts are minimally invasive, allowing reduction and fixation of simple fractures from outside the body. In contrast, bone plates are internal devices that mount directly to bone to span a fracture.

Trauma to the torso may result in fracture of one or more ribs. Frequently, a simple rib fracture is nondisplaced, so that reduction and/or internal fixation of the fracture may not be required. However, in cases of more severe trauma to the chest, a single rib may be fractured more severely and/or multiple rib fractures may occur. With multiple rib fractures, a section of the thoracic wall may become detached from the rest of the chest wall, a condition known to medical practitioners as "flail chest". A flail chest condition often results in paradoxical motion of the injured area, in which the freely floating thoracic section is drawn in during inspiration, and pushed out during expiration. This condition may result in severe respiratory distress, possibly requiring the patient to be sedated and/or intubated during early stages of healing. Fixing single or multiple rib fractures internally may alleviate paradoxical motion, reduce pain, and/or help to prevent secondary injuries.

Internal fixation of a rib fracture may be accomplished using a bone plate to span the fracture. A bone plate suitable for treating fractured ribs may be custom-contoured (i.e., bent) by a surgeon to conform to a region of a rib spanning a fracture, and then fastened to the rib on both sides of the fracture. The plate thus fixes the rib to permit healing. The plate may be fastened to the fractured rib using fasteners, such as bone screws, wires, and/or suture material, among others. Alternatively, a bone plate may be used that has prongs disposed along its length. The prongs may be crimped so that they grasp the rib to fasten the bone plate to the rib.

Each of these plating techniques may have disadvantages for rib fixation. For example, these techniques may not sufficiently stabilize the rib to provide adequate flexural and torsional support for the rib at the fracture site. Bone screws may not achieve adequate purchase in ribs to stabilize a bone plate because ribs are relatively thin and their bone density is low. Wires, suture material, and/or prongs also may not offer sufficient bone plate stabilization because they are not rigid enough. Each of these plating techniques thus may permit movement at the fracture with each breath, causing substantial pain and compromising the healing process. Furthermore, wires, suture material, and/or prongs may press on and damage a neurovascular bundle disposed on the inferior surface of ribs, if these fasteners are placed over this bundle during bone plate installation. Placement of these fasteners between the neurovascular bundle and bone still may damage the bundle and generally increases the time in surgery.

SUMMARY

The present teachings provide systems, including methods, apparatus, and kits, for fixing bones, such as rib bones, with bone plates.

BRIEF DESCRIPTION OF THE DRAWINGS

FIG. 1 is a view of an exemplary bone plate secured to and fixing a fractured rib bone, in accordance with aspects of the present teachings.

FIG. 2 is an exploded view of the bone plate of FIG. 1.

FIG. 3 is a view of an exemplary assembled configuration for components of the bone plate of FIG. 1, in accordance with aspects of the present teachings.

FIG. 7 is a partially sectional view of a bone caliper being used to measure the thickness of a bone, in accordance with aspects of the present teachings.

FIG. 8 is a sectional view of a clip component of a bone plate received on a bending die, in accordance with aspects of the present teachings.

FIG. 9 is a partially sectional view of the clip component of FIG. 8 being pushed against the bending die of FIG. 8, to bend the clip component and adjust the contour of the clip component to fit a bone, in accordance with aspects of the present teachings.

FIG. 10 is a partially sectional view of the clip component of FIG. 9 received on a bone and defining a drilling path for a drill bit of a drill forming a hole in the bone between a pair of apertures of the clip component, with an adjustable depth stop being used to limit the depth of the drill bit in the bone, in accordance with aspects of the present teachings.

FIG. 11 is a partially sectional view of the clip component and bone of FIG. 10 after placement of a bone screw through the bone and between the pair of apertures to secure the clip component to the bone, in accordance with aspects of the present teachings.

FIG. 14 is a view of another exemplary bone plate for fixing a fractured rib bone, with components of the bone plate disposed in an exemplary assembled configuration, in accordance with aspects of the present teachings.

FIG. 15 is a view of yet another exemplary bone plate for fixing a fractured rib bone, with components of the bone plate disposed in an exemplary assembled configuration and corresponding to in structure to plate components of FIGS. 1-4, in accordance with aspects of the present teachings.

FIG. 16 is a view of still another exemplary bone plate for fixing a fractured rib bone, with the bone plate configured as a unitary version of the bone plate of FIGS. 1-4, in accordance with aspects of the present teachings.

DETAILED DESCRIPTION

Figure 4:
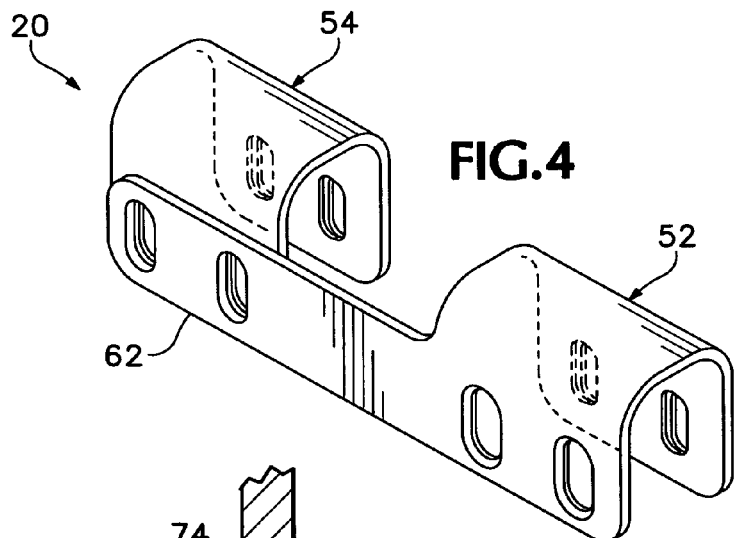
FIG. 4 is a view of an alternative exemplary assembled configuration for the components of the bone plate of FIG. 1, in accordance with aspects of the present teachings.

The present teachings provide systems, including methods, apparatus, and kits, for fixing bones, such as rib bones, with bone plates. The bone plates may include at least one clip portion configured to be received on a bone so that the clip portion wraps at least partially around the bone and extends at least to generally opposing surfaces of the bone. The clip portion may include at least one aperture for receiving a fastener, such as a bone screw, placed into bone. In some embodiments, the clip portion may include one or more pairs of aligned apertures for receiving a fastener placed through the bone and extending between the aligned apertures. In some examples, at least one of the aligned apertures may be a locking aperture that restricts axial movement of the fastener. The locking aperture may be circular and/or elongate, with a thread or an offset lip, among others, to engage the fastener. The bone plates may include at least one spanning portion configured to extend from the clip portion, generally along the bone, so that a fracture or other bone discontinuity is spanned by the plates. In some examples, the bone plates, when installed on bone, may include at least two clip portions connected by a spanning portion. The clip portions and the spanning portion may be formed unitarily in a single plate component or may be formed by two or more plate components that may be assembled on (and/or off) the bone. The bone plates of the present teachings may be secured more effectively to bones, such as fractured ribs, to provide improved stabilization of the bones, better healing, less pain, and/or less damage to associated soft tissue.

The bone plates may be part of a kit for fixing bones. The kit may include, for example, one or more plates and/or plate components, fasteners for securing the plates to bone, and/or apparatus for measuring bone, bending plates/plate components to fit bone, forming holes in bone, and/or driving fasteners into bone, among others.

These and other aspects of the present teachings are described below, including, among others, (I) overview of the bone plates, (II) accessories and kits, (III) methods of using the bone plates, and (IV) examples.

I. Overview of the Bone Plates

FIG. 1 shows an exemplary bone plate 20 fixing a fractured rib bone 22. Bone plate 20 may include one or more clip portions 24, 26 received on the bone and wrapping at least partially around the bone. For example, in the present illustration, the clip portions have been received from the superior side of (from above) the rib bone to appose superior surface 28 and generally opposing surfaces 30, 32 (such as anterior and posterior, outward and inward, and/or medial and lateral surfaces, among others) of the rib bone. Each clip portion thus may include a pair of generally opposing arms 34, 36 extending from and connected by a bridge region 38 (see FIG. 2). Plate 20 also may include a spanning portion 40 extending generally axially along the bone and spanning a fracture 42 in the bone (see FIG. 1). The spanning portion may extend between the clip portions, to connect the clip portions.

Bone plate 20 may be secured to bone 22 using suitable fasteners, such as bone screws 44. The bone plate thus may define one or more apertures 46 for receiving the bone screws. The apertures may be disposed so that the bone plate can be secured with bone screws to bone pieces 48, 50 created by fracture 42 and disposed on opposing sides of the fracture.

FIG. 2 shows bone plate 20 before assembly, and FIGS. 3 and 4 show bone plate 20 after assembly into different configurations. The bone plate may be unitary or may include two or more plate components 52, 54 configured to be secured to one another and to bone. In some examples, each plate component may include a clip portion, and one or more plate components may include a spanning portion. A spanning portion may be connected to a clip portion unitarily in a plate component, as shown for component 52. Alternatively, or in addition, a spanning portion in a first plate component may be connected to a clip portion in a second plate component with a fastening mechanism. For example, the plate components may be configured to be placed into an overlapped configuration, shown at 56 in FIG. 3, so that an outer surface 58 of component 52 overlaps and abuts an inner surface 60 of component 54 (see FIG. 2). Alternatively, as shown in FIG. 4, or in addition, the plate components may be overlapped so that an inner surface of component 52 overlaps and abuts an outer surface of component 54. Accordingly, a distal end region 62 of the spanning portion may be interposed between a clip portion and bone (see FIG. 3), or may be spaced from bone by the clip portion (see FIG. 4). The placement shown in FIG. 4 may space the inner surface of the spanning portion from the underlying bone and thus may be used, for example, in situations where it is desirable to leave a small gap between the bone plate and the bone in the vicinity of a fracture. This may promote a relatively greater blood supply to the bone near the fracture, possibly leading to faster healing in some cases.

Each of the plate components may include one or more apertures configured to be aligned with, and generally abut, a corresponding aperture of the other component, such as abutted aperture pair 64, 66 (see FIGS. 2 and 3). In some examples, the bone plates may have at least two pairs of abutted apertures provided by overlapping plate components, which may secure the plate components to one another more effectively. In some examples, two or more alternative alignments of abutted apertures may be permitted, so that the spacing between clip portions can be selected from two or more possible spacings (see Example 1).

Figure 5A:
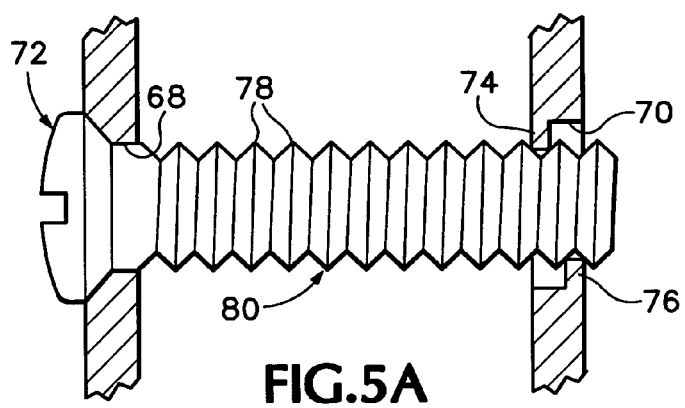
FIG. 5A is a fragmentary sectional view of the bone plate of FIG. 1 without the rib bone, taken generally along line 5A-5A of FIG. 1, and illustrating a bone screw extending through a pair of aligned plate apertures including an exemplary locking aperture, in accordance with aspects of the present teachings.

Each clip portion may include one or more pairs of aligned apertures configured to be disposed adjacent generally opposing surfaces of a bone. For example, spaced aperture pair 68, 70 (see FIG. 2) may be configured to receive a bone screw 72 that extends through bone apertures of the aperture pair (see FIGS. 1 and 5A). In some examples, the clip portion may include at least two spaced pairs of apertures, to secure the clip portion to bone more effectively and thus provide better stabilization of bone. Alternatively, the fastener may extend through a single aperture or an abutted aperture pair into bone, but not completely through the bone. In any case, one or more of the apertures may be a locking aperture, that is, an aperture configured to engage the fastener so that axial movement of the fastener in both axial directions is restricted.

In the present illustration, distal aperture 70 is an elongate locking aperture (a locking slot) having an offset lip with offset ridges 74, 76 (an offset lip) formed by opposing walls of this elongate aperture. The ridges may be at least partially linear, extending parallel to the long axis of the aperture. Ridges 74, 76 may be configured to be received between adjacent (or nonadjacent) thread segments 78 of a thread 80 formed on the shaft of bone screw 72, so that engagement between ridges 74, 76 (or one ridge) and the thread segments locks the bone screw to the plate. Furthermore, rotation of the bone screw after the head of the bone screw has engaged the plate may urge the arms of clip portion toward each other, because the shaft of the screw can advance relative to the locking aperture 70, whereas the head of the screw cannot advance relative to proximal aperture 68. Accordingly, this rotation may adjust the spacing of the arms and/or compression of the bone by the clip portion.

Figure 5B:
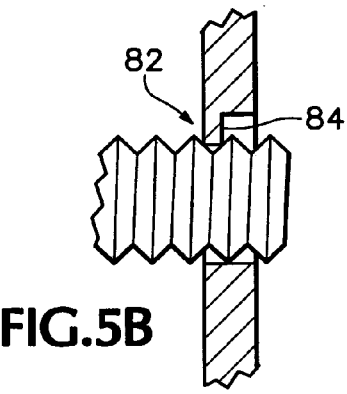
FIG. 5B is a fragmentary sectional view of another exemplary locking aperture engaged with a bone screw, in accordance with aspects of the present teachings.

FIG. 5B shows another example of an elongate locking aperture 82 receiving a bone screw. In this example, only one of two opposing walls of the locking aperture has a ridge 84 configured to be received between thread segments of the bone screw.

Figure 6:
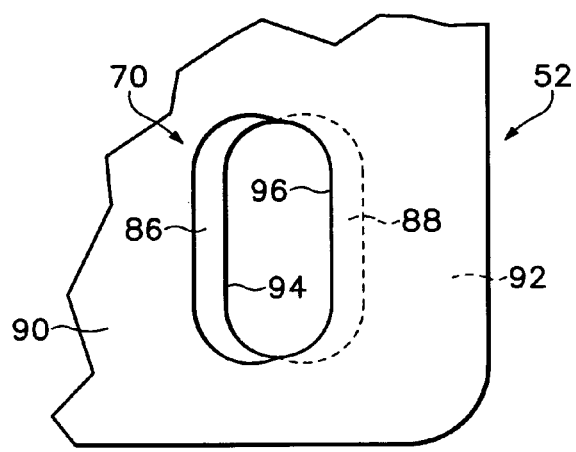
FIG. 6 is a view of a portion of the bone plate of FIGS. 1-4, as indicated in FIG. 2, and including the locking aperture of the pair of apertures of FIG. 5A, in accordance with aspects of the present teachings.

FIG. 6 shows a portion of the bone plate including locking aperture 70. The locking aperture may be formed from an oval aperture flanked by recessed and/or thinned regions 86, 88 of the plate formed on inner and outer surfaces 90, 92 of the plate, respectively, and with opposing walls 94, 96 of the aperture. Alternatively, only one of the surfaces may be recessed, to form only one ridge or lip region to be received between thread segments (see FIG. 5B). Locking apertures, and particularly an aligned, spaced pair of apertures that include a locking feature, may secure the plate to the bone more effectively than a nonlocking aperture or aperture pair and thus may provide better fixation of the bone. Further aspects of locking apertures, particularly elongate locking apertures, are included in U.S. Provisional Patent Application Ser. No. 60/548,685, filed Feb. 26, 2004, which is incorporated herein by reference.

Further aspects of the bone plates are described in the following sub-sections, including, among others, (A) clip portions, (B) spanning portions, (C) apertures, and (D) plate components.

A. Clip Portions

The bone plates each may include one or more clip portions. A clip portion, as used herein, is any region of a plate configured to be received by a bone so that the clip portion is disposed adjacent generally opposing surfaces of the bone. Accordingly, the clip portion may extend in a generally circumferential direction at least partially (or completely) around a bone, to wrap at least partially (or completely) around the bone. The clip portion may extend along any suitable portion of a bone's circumference, such as about one-fourth to three-fourths.

A clip portion may have any suitable contour or shape. For example, the clip portion may match, at least substantially, a surface contour of a bone for which the clip portion is configured. In some examples, the clip portion may be generally U-shaped, V-shaped, or O-shaped, among others, with a generally curved and/or angular contour. The clip portion thus may contact the bone along any suitable extent of the inner surface of the clip portion. The clip portion may have first and second regions (the arms) configured to be disposed adjacent generally opposing bone surfaces, and a third region (the bridge region) extending between the first and second regions. In some examples, the clip portion may be included in a plate or plate component having a fourth region (the spanning portion) extending from the clip portion, such as from only one of the first and second regions. In some examples, both the arms (or only one arm) and the bridge region of the clip portion may contact the bone. In some examples, the bridge region may be spaced from the bone. The clip portion may be contoured before and/or during installation according to the shape of bone (see Section III).

A clip portion may be configured to be received on and contact any suitable side(s) of a bone. The clip portion thus may be received from a superior, inferior, anterior, posterior, lateral, and/or medial direction, among others, onto the bone. The bridge region of the clip portion thus may be positioned adjacent the corresponding surface of the bone or may be rotated after the clip portion is received so the bridge region is positioned adjacent a different surface of the bone. Furthermore, the arms of the clip portion may be configured to be disposed adjacent any suitable generally opposing bone surfaces, such as surfaces that are posterior and anterior, inward and outward, medial and lateral, superior and inferior, or a combination thereof. In exemplary embodiments, for the purposes of illustration, the clip portion may be received from a superior direction onto a rib. The bridge region of the clip portion thus may be disposed adjacent and/or in engagement with a superior surface of the rib, and the arms of the clip portion thus may be disposed adjacent and/or in engagement with inward (internal) and outward external) surfaces of the rib, generally anterior and posterior surfaces and/or medial and lateral surfaces. Two or more clip portions may have the same or different orientations on bone, to appose and/or contact the same or different sides/surfaces of the bone.

A clip portion may have any suitable spacing, structure, and disposition of its arms. Generally the arms may be spaced about the same as the distance between generally opposing surfaces of a target bone, that is, about the width, thickness, and/or diameter of the bone where the clip portion will be disposed. However, in some examples, the arms may be spaced somewhat greater than this width or diameter, at least when the clip portion is first placed on bone, to facilitate placement. Alternatively, the arms may be spaced somewhat less than this width or diameter, so that the clip portion may be "snapped" onto bone. The arms may be generally linear or may bend along their long axes. Furthermore, the arms may be nontwisted or may twist. The arms may be at least substantially parallel, or may diverge or converge toward their distal ends (spaced from the bridge region).

A clip portion may have any suitable width. The width of the clip portion may be measured between opposing edges of the arms and/or the bridge region, for example, generally parallel to the long axis of the bone when the clip portion is disposed on bone. The width may be substantially greater than the thickness of the bone plate (generally at least about twice the thickness), so that the clip portion is plate-like rather than rod-like. The width may be generally constant within each arm and/or within the bridge region. Alternatively the width may vary within one or both arms, between the arms, within the bridge region, or between the arms and the bridge region. For example, the arms may taper away from the bridge region. Alternatively, or in addition, the bridge region may be narrower than the arms, to facilitate bending the bridge region (e.g., to facilitate adjustment of the spacing of the arms), or the arms may be narrower than the bridge region (e.g., to facilitate adjustment by bending the arms). In some embodiments, the clip portion may include one or more narrowed regions, at which the clip portion may be selectively bent, such as within one or both arms or the bridge region, and/or at a junctions between a arm and the bridge region. Exemplary widths of the bridge region include about 2-50 mm or about 5-20 mm, among others.

A clip portion may have any suitable thickness. The thickness may be selected based on various considerations, such as reducing the profile of the clip portion on bone, providing a sufficient strength to fix bone, bendability, providing a sufficient thickness to form an offset lip or a thread in an aperture for engaging a fastener thread, and/or the like. Exemplary thicknesses include about 0.2-3 mm or about 0.5-2 mm, among others.

A clip portion may have any suitable number, shape, and arrangement of apertures. The clip portion may have no apertures or may have one or more apertures. Each aperture may be circular, square, elongate (such as oval, elliptical, rectangular, etc.), and/or the like. Each aperture may include or lack a counterbore. The aperture may be locking or nonlocking. Locking apertures generally include a retention structure to engage a fastener, such as through a thread of the fastener, and restrict axial movement of the fastener in both axial directions. The structure may be one or more ridges formed by the wall of a locking aperture. The ridges may be generally helical, to form a thread, at least partially linear to form a locking slot, and/or the like. Further aspects of locking slots are described above and in U.S. Provisional Patent Application Ser. No. 60/548,685, filed Feb. 26, 2004, which is incorporated herein by reference. The apertures may be disposed in the arms and/or the bridge region of the clip portion. If two or more apertures are included in a clip portion, the apertures may be arrayed across the width and/or along the length of one or more arms and/or the bridge region, and/or may have a staggered disposition. In some examples, one or more pairs of apertures may be aligned, that is, configured to receive the same fastener with each aperture of the pair. Apertures of an aligned pair may be disposed in the arms and/or in the bridge region and one arm, among others. Each aligned pair of apertures may include zero, one, or two locking apertures. Apertures of an aligned pair may have the same general shape, such as oval or circular, or may have different shapes, such as oval and circular, among others. Furthermore, apertures of an aligned pair may be of generally the same size, such as about the same length and/or width, or may have different lengths and/or widths. In exemplary embodiments, apertures of an aligned pair may be have about the same length, with one of the apertures being narrower than the other to create retention structure to lock a fastener in position. Providing two or more aligned pairs of apertures in the clip portion may lead to enhanced torsional and/or bending stability of the fracture site, by inhibiting rotation of the clip portion relative to the bone. The thickness of the bone plate adjacent the aperture(s) (in the clip portion and/or other portions of the plate) may be generally the same as, less than, or greater than the thickness of the plate away from the aperture(s). Plate thinning near the apertures may provide a recess for reducing the profile of fasteners placed in the apertures, and plate thickening near the apertures may reinforce the aperture.

B. Spanning Portions

The bone plates each may include one or more spanning portions. A spanning portion, as used herein, is any region of a bone plate configured to extend between two or more clip portions of the plate. Accordingly, the spanning portion may extend in a generally axial direction along a bone, generally spanning a discontinuity (such as a fracture) of the bone.

A spanning portion may have any suitable contour or shape. For example, the spanning portion may match, at least substantially, a surface contour of a bone for which the spanning portion is configured. For example, the spanning portion may be generally linear or bent as it extends between clip portions (along its spanning axis). If bent, the spanning portion may have a concave and/or convex bend along its inner surface, based, for example, on the surface contour of a bone for which the spanning portion is configured. The spanning portion also may be linear or curved across its width (and on its inner and/or outer surfaces), based, for example, on a local circumferential contour of the bone that is linear or curved, respectively. The spanning portion thus may be configured to contact the bone along any suitable extent of its inner surface. The spanning portion may be bent before and/or during installation according to the shape of bone or may be nonbent.

A spanning portion may be configured to be received on any suitable side/surface of a bone. The spanning portion thus may be disposed adjacent a superior, inferior, anterior, posterior, lateral, and/or medial bone surface, among others. In some examples, the spanning portion may be disposed adjacent only one surface of a bone, such as superior, inferior, outward (external), or inward (internal; e.g., an inward surface of a rib bone). Outward and inward surfaces, as used herein, refer the generally opposing surfaces of the ribs that are flanked by superior and inferior rib bone surfaces. In some examples, the spanning portion may be disposed adjacent and may contact two or more bone surfaces, such as superior and outward surfaces; superior and inward surfaces; superior, inward, and outward surfaces; and/or the like. The spanning portion thus may extend along bone from any suitable region(s) of each clip portion. Exemplary regions include only one arm, one arm and the bridge region, two arms, or two arms and the bridge region of the clip portion.

A spanning portion may have any suitable dimensions, such as length (L; generally measured along the spanning dimension and along a bone), width (W; generally measured), and thickness (T). Here, $L \geqq W > T$. The length may be measured along the spanning dimension, that is, along a bone with the bone plate installed. The width may be measured along the circumferential dimension, that is, around the bone with the bone plate installed. However, in some examples, the spanning dimension may be about the same as or less than the circumferential dimension. For example, the spanning portion may be relatively short and the clip portions relatively long, as measured along bone, or the clips portions may be secured directly to one another or formed unitarily, without a distinct spanning portion. The width and/or circumferential dimension of the spanning portion may be determined, at least partially, by the extent each clip portion from which the spanning portion extends, as described above. Furthermore, the width and/or circumferential dimension of the spanning portion may be substantially greater than the thickness of the bone plate (generally at least about twice the thickness), so that the spanning portion is plate-like rather than rod-like. The width may be generally constant or may vary as the spanning portion extends between the clip portions. In some embodiments, the spanning portion may include one or more narrowed regions at which the spanning portion may be selectively bent. Exemplary average widths of the spanning portion include about 2-30 mm or about 5-20 mm, among others. The thickness of the spanning portion may be about the same as, less than, or greater than the thickness of the clip portions. The thickness may be selected based on various considerations, such as reducing the profile of the spanning portion above bone, a sufficient strength to fix bone, bendability, and/or the like. The thickness may be constant or may vary, for example, at regions of overlap with another plate component and/or near apertures (as described above). Exemplary thicknesses of the spanning portion include about 0.2-3 mm or about 0.5-2 mm, among others.

A spanning portion may have any suitable number, shape, and arrangement of apertures. The spanning portion may have no apertures or may have one or more apertures. Each aperture may be circular, square, elongate (such as oval, elliptical, rectangular, etc.), and/or the like. Each aperture may include or lack a counterbore. The aperture may be locking or nonlocking, as described above for clip portions. If two or more apertures are included in a spanning portion, the apertures may be arrayed across the width and/or along the length, and/or may have a staggered disposition, among others. In some examples, one or more apertures of the spanning portion may be configured to be aligned with, and generally abut, corresponding apertures of a clip portion. Accordingly, the spanning portion may have two or more apertures that align with two or more apertures of a clip portion, to facilitate securing the spanning portion to the clip portion with fasteners. In some examples, the spanning portion may have three or more apertures configured to permit the clip portion to be aligned alternatively with two or more pairs of the apertures. In some examples, the spanning portion may have apertures configured so that two or more clip portions can be secured to the spanning portion with fasteners at nonoverlapping positions of the spanning portion. These apertures may be arranged for securing the clip portions to opposing end regions of the spanning portion and/or to one or more intermediate regions of the spanning portion, among others.

C. Apertures

The bone plates may have apertures to perform any suitable functions. For instance, apertures may be configured to receive fasteners for securing plate components to each other and/or to a fractured bone. Alternatively, or in addition, apertures may be provided that are adapted to alter the local rigidity of the plates and/or to facilitate blood flow to the fracture to promote healing.

The apertures may have any suitable geometry(ies). For example, some apertures may be substantially oval, whereas other apertures may be substantially circular. Oval apertures may be used, for example, to permit flexibility in placement of a fastener in a range of translational and/or angular positions within the aperture. Furthermore, oval apertures may permit a bone plate and/or plate component to slide parallel to the long axis of an oval aperture, to facilitate adjustment of the plate and/or plate component position, after a fastener has been received in the aperture and in bone. Oval apertures also may function as compression slots that bias a fastener toward or away from a discontinuity in the underlying bone. Circular apertures may be locking (such as threaded) or nonlocking apertures. Alternatively, or in addition, to engage a threaded fastener, the circular (or other) apertures may be configured such that a nut, clip, and/or other retaining device can engage an end or other portion of the fastener where it extends from the aperture. Furthermore, circular apertures may be used to receive additional fasteners, such as pins, after the plate is finally positioned. The apertures may include counterbores that allow the head of fasteners to have a reduced profile above the bone plate and/or to lie substantially flush with the top surface of the plate.

The apertures of the bone plates may have various sizes, depending on their intended usage. For example, if used with fasteners, the apertures may be sized for different sized fasteners, such as bone screws with diameters of 2.1, 2.7, 3.5, and/or 4.0 mm. Generally, the larger the plate, the larger the number (and/or size) of apertures, so that larger plates may allow relatively larger numbers of screws (and/or larger screws) to be used. Thus, bone plates used to treat larger bones may include relatively larger apertures, or relatively larger numbers of apertures. Providing relatively greater numbers of apertures to accept bone fasteners may lead to relatively greater torsional and/or bending stability of the fracture site, when the bone plate is installed on a bone. The apertures in a particular plate may have a hybrid arrangement, such as a size of 3.5 mm in one region of the plate, and a size of 2.7 mm in another region of the plate, among others.

In general, the apertures may have any suitable arrangement in the plate. For example, the apertures may be clustered together at end regions of the bone plate, to increase the number of screws that can be used to fix the associated segment(s) of bone(s) via the plate, or they may be spaced substantially evenly along the length of the plate, including regions of the plate that do not have a corresponding opposing portion disposed adjacent an opposing side of the bone. The apertures may be positioned side-by-side, with preceding and/or subsequent apertures positioned along a common axis of the plate or arranged in a two-dimensional pattern, increasing the density of screws that may be used.

D. Plate Components and Fasteners

The bone plates may have any suitable number of plate components. For example, the bone plates may be unitary or may have two or more pieces configured to be secured to one another and to bone with fasteners. In some embodiments, first and second components of a bone plate may be supplemented by a third, fourth, or even higher number analogous component, with each component independently formed integrally or separately from each other component. The various components of the plate may be used alone or in any suitable combination, as appropriate or desired for a given application. The various components also may be configured to have the same or different shapes and sizes.

The components of a bone plate may be configured to be assembled in an overlapping configuration. The overlapping configuration may abut an inner surface region of one of the components with an outer surface of another of the components. The regions of overlap of the components may be geometrically similar to adjacent nonoverlapping regions, or they may be specially configured to facilitate the overlap. For example, the thickness of one or both components may be reduced in the region of overlap. In some embodiments the overlapping regions may be beveled, and/or tapered, so that the boundary between the overlapping and nonoverlapping regions of a plate component may be relatively smooth along the inner (bone-facing) and/or outer (non-bone-facing) surfaces of the bone plate. Alternatively, or in addition, the surfaces of the plates that contact one another may be configured and/or treated (e.g., roughened) to reduce slippage or the like. Exemplary configurations to reduce slippage may include one or more complementary depressions and projections (such as pins and holes) formed on mating surfaces of the plate components.

The components of a bone plate may be secured to one another and to bone with any suitable fasteners and at any suitable time. The fasteners generally comprise any fastener mechanism, including screws, bolts, nuts, pins, hooks, suture material, and/or wires, among others. (In some cases, the fasteners may include adhesives and/or other nonmechanical mechanisms.) Exemplary fasteners may be machine screws to secure plate components to one another and/or bone screws. Each bone screw may be received in bone and in a single aperture of the bone plate, a pair of aligned apertures disposed adjacent generally opposing bone surface (such as aligned apertures of a clip portion), and/or three or more aligned apertures provided by two or more plate components. The components may be secured to each other off of bone and/or on bone.

The bone screws may be unicortical, bicortical, and/or cancellous bone screws, among others. Unicortical and bicortical bone screws typically have relatively small threads for use in hard bone, such as near the middle of a clavicle, whereas cancellous bone screws typically have relatively larger threads for use in soft bone, such as in a rib. Unicortical bone screws penetrate the bone cortex once, adjacent a single surface of the bone. Bicortical bone screws penetrate the bone cortex at one surface of the bone, pass through the bone, and then penetrate the cortex again adjacent a generally opposing surface of the bone. Generally, unicortical screws provide less support than bicortical screws, because they penetrate less cortex.

The size and shape of the fasteners may be selected based on the size and shape of the apertures or vice versa. An exemplary fastener is a threaded bone screw having features specifically adapted to fit the plate construction. The bone screw may have a head wider than the width or diameter of an aperture defined by the bone plate, a length approximating the width of the bridge region of a clip portion (and/or of bone), and a thread configured to engage a lip or thread of an aperture of the bone plate.

E. Plate Materials

The bone plates may be formed of any suitable material(s). Generally, the bone plates should be at least as stiff and strong as the section of bone spanned by the plates (typically, as stiff and strong as the bone in the absence of any discontinuity), yet flexible, bendable, and/or springy enough not to strain the bone significantly. Suitable materials for forming the bone plates may include metal, polymer, plastic, ceramic, composite, and/or the like. Such materials may be biocompatible. Exemplary biocompatible materials may include metals/metal alloys (for example, titanium or titanium alloys; alloys with cobalt, chromium, and/or molybdenum; stainless steel; etc.) and/or bioresorbable materials (such as polygalactic acid (PGA), polylactic acid (PLA), polycaprolactones, polydioxanones, copolymers thereof, etc.), among others.

II. Accessories and Kits

The bone plates described herein may be used with various accessories and/or may be supplied in a kit. These accessories may be used, alone or from a kit, during the preparation, installation, and/or removal of bone plates (including the associated fasteners), among others. Exemplary accessories may include bone calipers, dies, hole-forming devices, drivers, and/or the like. A bone caliper may be used to measure the size of a bone to be fixed. Measurement of the size may facilitate selection of a suitable bone plate/plate component(s), a suitable die for bending a bone plate/plate component(s), and/or suitable fasteners (such as by length) for securing the bone plate/plate component(s) to bone, among others. The die may permit a bone plate to be shaped pre- and/or intraoperatively, for example, by a surgeon installing the plate. Furthermore, the die may permit the bone plate to be shaped to conform at least substantially to a particular fractured bone (or segment of a bone), such as a fractured rib. A hole-forming device such as a drill with an adjustable drill stop may be used to drill a hole in the bone to a desired depth, based, for example, on the measured size of the bone. A driver such as a screwdriver may be used to install and/or remove fasteners. Further aspects of accessories and kits are described below.

A. Bone Calipers

The bone plates optionally may be used with any suitable measuring devices, such as bone calipers, to measure one or more dimensions of a bone to be fixed. For example, FIG. 7 shows an exemplary bone caliper 110 being used to measure the thickness of a rib bone 112. Caliper 110 may include an arcuate end portion 114, which is configured to conform to a preselected (e.g., superior) surface of the rib bone, and which also may be configured to wrap partially around another (e.g., posterior) surface of the bone. More generally, end portion 114 (and other portions) of the caliper may be adapted to conform to the size and/or shape of any desired bone(s), so that a similar instrument may be used to measure the thickness of various bones other than ribs. Caliper 110 also may include a clamping member 116, which may be attached to a movable measurement scale 118. Once end portion 114 of the caliper has been placed adjacent the bone being measured, scale 118 may be moved until member 116 makes contact with the bone. Then, as indicated at 120, the approximate thickness of the bone may be read from the scale.

The dimensions of a fractured bone, measured as above, or otherwise known, may be used for any suitable purpose. For example, the dimensions may be used to select an appropriate bone plate or plate component from a set of plates or components, and/or they may be used to pre- or intraoperatively shape a bone plate to fit the bone.

B. Bending Dies and Hole-Forming Tools

The bone plates optionally may be used with any suitable dies and/or hole-forming tools. The dies may be configured to bend the plates from a planar configuration and/or to adjust the shape of the plates from a bent configuration. The hole-forming tools may be used to form holes in bone and/or in bone plates, generally to facilitate placement of fasteners.

FIGS. 8 and 9 show an exemplary bending die 130 being used to shape a bone plate 132, or a component thereof, to fit a rib bone. In FIG. 8, the die has received the plate in a partially bent configuration, and in FIG. 9, the die is being bent with application of a compressive force through compression members 134, 136.

Die 130 may have a size and shape that approximates one or more cross sectional dimensions of a rib bone, to facilitate contouring a bone plate/plate component to match these dimensions at least substantially. In particular, the die may facilitate contouring plate component 132 to match the size (e.g., thickness) of the bone, and to match the shape or curvature of a preselected (e.g., superior) surface of the bone. To contour a bone plate, or a component thereof, using the bending die, a flat or partially contoured plate may be shaped around the die manually. Alternatively, or in addition, a tool such as pliers or another clamping mechanism may be used to add precision and/or mechanical advantage during bending. In some embodiments, the die may be narrower and tapered more than the actual shape of the bone, so that bone plates shaped by the die may be configured to compress the bone slightly even before being fixed into position on the bone. Die 130 may be configured to approximate the size and shape of a rib bone; however, more generally, dies may be provided that facilitate contouring of plates to match the dimensions of other bones, such as clavicles, among others.

FIGS. 10 and 11 show the use of a drill, drill stop, and fastener for mounting a bone plate to a bone.

FIG. 10 shows a drill 140 including a drill bit 142 drilling through a bone 144. Bit 142 has been guided into bone through an aperture 146 of bone plate 132, while the bone plate is in position on the bone. The drill bit may include an elongate shaft 148, and a drilling tip 150 attached to the shaft. An adjustable depth stop 152 may be disposed and secured along the drill bit at a selected axial position of the bit, so that a suitable length of the drilling tip extends beyond the depth stop. Securing the depth stop to the bit in this manner prevents the bit from penetrating the bone beyond a desired depth, and may inhibit damage to tissue behind the bone, when the bone is drilled. Depth stop 152 may be secured to the bit by any suitable mechanism, such as an Allen bolt 154, and/or engagement with grooves or slots provided along the length of shaft 148. The shaft of the drill bit may be provided with a scale, generally indicated at 156, for positioning the depth stop at predefined distances from the distal tip of the drill bit. Alternatively, or in addition, the depth stop may be positioned by measuring a desired distance from the distal tip with any standard measuring device, such as a ruler, tape measure, or caliper, among others.

FIG. 11 shows bone plate 132 attached to bone 144 with a threaded bone screw 160, in the hole formed by the drill bit (see FIG. 10). Screw 160 may be selected based on the measured thickness of the bone. In particular, a threaded screw may be chosen that is long enough to reach and engage a locking aperture 162 adjacent an opposing surface 164 of the bone, but not so long that a distal end 166 of the screw protrudes, or protrudes excessively, through the bone plate. This configuration may allow the screw to engage the plate securely and compress the plate and the underlying bone, while reducing or eliminating unnecessary physiological damage or discomfort to the patient.

Figure 12:
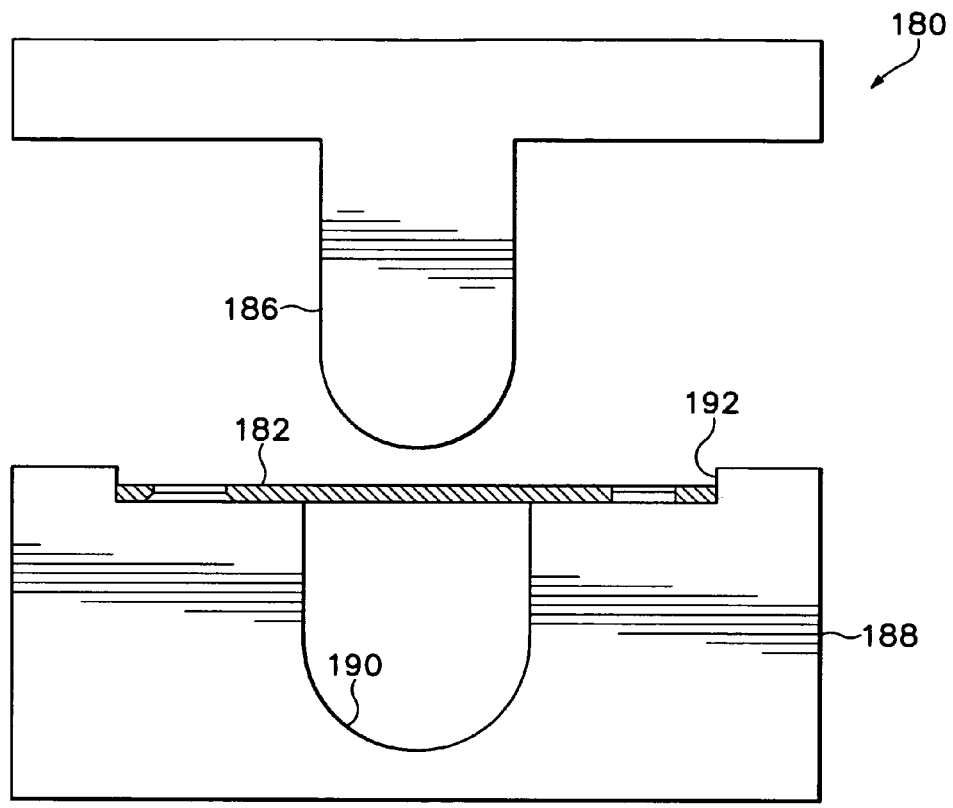
FIG. 12 is a partially sectional view of a die assembly holding a plate member before the plate member is bent into a clip component, in accordance with aspects of the present teachings.
Figure 13:
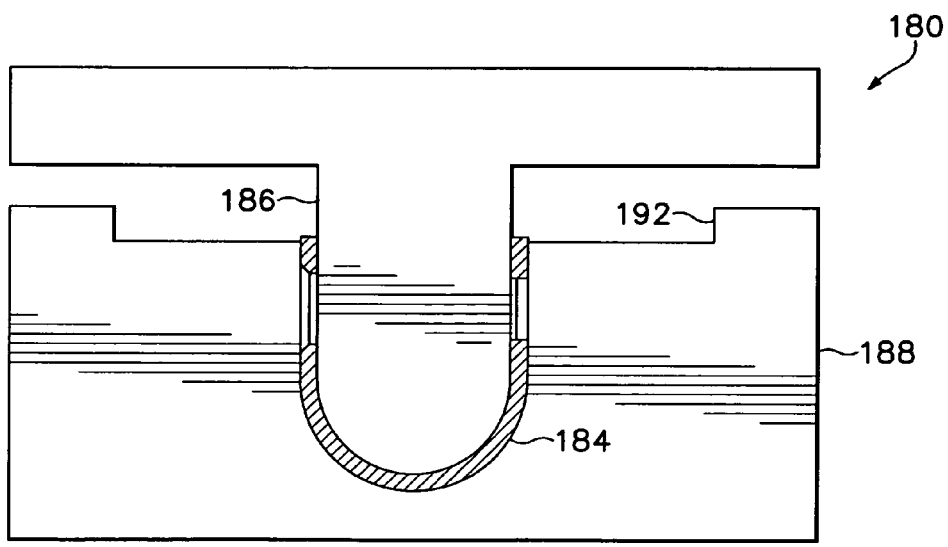
FIG. 13 is a partially sectional view of the die assembly and plate member of FIG. 12 after the die assembly has been used to bend the plate member into a clip component, in accordance with aspects of the present teachings.

FIGS. 12 and 13 show an exemplary die assembly 180 before (FIG. 12) and after (FIG. 13) bending a plate member 182 into a clip portion 184. The die assembly may include an anvil 186 configured to fit into a receiver 188, with a gap sufficient to accommodate the plate member disposed between the anvil and the receiver. The anvil may be configured to be pressed into the receiver, such as with a clamp device or one or more blows from a hammer, among others. The receiver may be configured to position the plate member over a cavity 190 of the receiver. For example, the receiver may include a recessed structure 192, projections, or the like, to restrict lateral movement of the plate member before and/or during bending.

A bending die and/or die assembly may be adjustable and/or available as part of a set to accommodate bones of different sizes and shapes. Thus, while the exemplary dies described above may have fixed dimensions, in some embodiments these dies may be internally adjustable, for example, using one or more internal set screws, such that the overall size and/or shape of the die may be set by adjusting the set screws. Alternatively, a plurality of bending dies, fixed and/or adjustable, may be provided for each size, shape, and/or type of bone, so that bone plate components may be shaped to any desired size. The range of sizes of the dies provided may correspond to an expected range in sizes of the type of bone being treated. For example, for contouring bone plates suitable for rib bones, dies may be provided that have maximum widths ranging between approximately 0.10 inches (about 2.5 mm) and approximately 0.50 inches (about 13 mm), or between approximately 0.15 inches (about 3.8 mm) and approximately 0.38 inches (about 10 mm), among others.

C. Kits

The bone plates, fasteners, accessories, etc. described above may be provided singly and/or as a kit, in combination with one another and/or yet other accessories. The kits may include, among others, a set of bone plates constructed to fit various bones and/or regions of bones. For example, the kit may include plates configured to fit ribs and/or clavicles of various sizes and shapes, as well as to fit on various regions of a rib and/or a clavicle. In addition, the kit may include instrumentation for measuring one or more dimensions of the bone, and/or for intraoperatively bending and installing a bone plate (or portion thereof). For example, the instrumentation may include a bone caliper, an adjustable bending die, and/or a drill bit including a depth stop. The kit also may include a case or organizer, instructions, mounting hardware such as bone screws of various lengths and/or diameters, drivers such as screwdrivers for installing and/or removing mounting hardware, and/or other accessories related to bone plates.

III. Methods of Using the Bone Plates

Bone plates of the present teachings may be installed on bones by any suitable methods. This section describes exemplary method steps that may be suitable to fix bones with the bone plates. These steps and those described elsewhere in the present teachings may be performed in any suitable order, in any suitable combination, and any suitable number of times.

A bone to be fixed may be selected. Exemplary bones may include ribs and/or clavicles. Other exemplary bones may include bones of the arms (radius, ulna, humerus), legs (femur, tibia, fibula, patella), hands/wrists (e.g., phalanges, metacarpals, and carpals), feet/ankles (e.g., phalanges, metatarsals, and tarsals), vertebrae, scapulas, pelvic bones, and/or cranial bones, among others. The bone may be selected from any suitable species, including human, equine, canine, and/or feline species, among others. The bone may lack or include a discontinuity, which may occur naturally and/or as a result of injury, disease, and/or surgical intervention, among others. Accordingly, exemplary discontinuities for use with the bone plates described herein may include joints, fractures (breaks in bones), osteotomies (cuts in bones), and/or nonunions (for example, produced by injury, disease, or a birth defect), among others.

A discontinuity in the bone may be reduced. For example, a fractured bone may be set. Reduction of the discontinuity may be performed before, during, and/or after a bone plate is secured to the bone.

An aspect of the bone may be measured, generally in the vicinity of the discontinuity. Measurement may be performed with any suitable measuring device or method, such as calipers, a ruler, a tape measure, a fluoroscope (e.g., by fluorography), and/or the like. The aspect may correspond to a characteristic dimension (such as thickness, width, length, and/or diameter, among others). Alternatively, or in addition, the aspect may correspond to a curvature or surface contour of the bone, among others.

A bone plate may be selected for installation on the bone. The bone plate may be selected from a set of available bone plates. For example, the set may include bone plates with different leg-to-leg spacings and/or radii of curvature for their clamp portions and/or different lengths of spanning portions, among others. Selection may be performed based on the type, size, and/or contour of the bone, among others, and thus may be based on the type of bone and/or on a measured, average, and/or expected aspect (such as thickness) of the bone. The bone plate may be pre-bent for the bone selected and/or may be custom contoured for a particular bone, bone region, and/or for the particular anatomy of the patient. Custom contouring (generally, bending) may be performed pre- and/or intra-operatively by hand, with a bending tool, and/or with a die, among others.

The bone plate selected may be positioned on bone. The step of positioning may include placing a unitary bone plate or two or more plate components on the bone, from any suitable direction. In exemplary embodiments, the bone plate and/or a plate component(s) may be placed on a bone from above the bone (from a superior direction). With two or more plate components, the plate components may be placed on bone in any suitable order. In some embodiments, a first plate component including a first clip portion and a spanning portion may be placed onto bone, and then a second plate component including a second clip portion may be placed onto bone, overlapping and outside of the spanning portion. In some embodiments, this order and/or disposition of placement may be reversed. Furthermore, additional plate components also may be placed on the bone. In some examples, a clip portion of the bone plate may have a leg-to-leg spacing that is less than the thickness/width/diameter of the bone, so the clip portion "snaps" in place on the bone.

The selection and/or positioning of bone plates, as described in the present teachings, may take advantage of the differential characteristics and/or accessibility of different portions or surfaces of a given bone. For example, a bone plate with clip and spanning portions may be selected and positioned such that the spanning portion and/or clip portion (or a region(s) thereof, such as an arm and/or bridge region) is located along a more accessible and/or less vascularized or innervated portion of the bone, such as the outward or anterior surface of a rib. In this way, relatively more bone plate is positioned adjacent more accessible and/or less sensitive portions of the bone, and relatively less bone plate (e.g., just one or two arms of the clip portion(s)) is positioned adjacent less accessible and/or more sensitive portions of the bone.

One or more holes may be formed in the bone. The holes may be formed with a hole-forming device, such as a drill, a punch, and/or a self-drilling bone screw, among others. If formed with a drill, a drill stop, such as the drill stop of FIG. 10, may be used to prevent forming a hole that is too deep, which may cause unnecessary tissue damage and/or remove bone unnecessarily. The holes may be formed before or after one or more plate components are positioned on the bone. If formed after a plate component is positioned on the bone, the hole may be formed in alignment with one aperture, or two, three, or more aligned apertures of one plate component, or two or more overlapping plate components. Accordingly, the aperture(s) may function as a guide for the hole-forming tool. The holes may extend from an aperture into bone and/or through bone. In some examples, a hole may extend between a pair of aligned, spaced apertures of a clip portion.

The bone plate may be secured to the bone with one or more fasteners, such as bone screws. One or more fasteners thus may be selected. The fasteners may be selected, for example, to have a shaft diameter less than the width/diameter of a target aperture, and to have a thread configuration corresponding to the size/offset of an aperture lip (for an elongate locking aperture) or to the pitch of an aperture thread (for a circular locking aperture). The fasteners also or alternatively may be selected to have a length (particularly a shaft length) about the same as the measured or expected thickness/width/diameter of the bone. The fasteners may be placed through apertures and into pre-formed holes or may form holes themselves. The fasteners may engage a plate component adjacent one side of the bone and/or adjacent generally opposing surfaces of the bone, among others. Each fastener may extend through a single plate component or two or more overlapping plate components. Accordingly, the fastener may secure two or more plate components together and/or to bone. In some examples, the fastener may lock to one or more plate components, adjacent only one side of the bone or adjacent each of two generally opposing surfaces of the bone. In some examples, the fastener may be tightened until generally opposing regions of a plate component or bone plate are compressed against the bone. The fasteners may be placed into apertures of the bone plate in any suitable order. For example, a first plate component may be partially or completely secured to the bone first, and then a second plate component secured to the bone, or the plate components may be secured to bone at least initially with the same fastener(s). The fasteners may be installed and/or removed by hand and/or with the assistance of a suitable driver, such as a screwdriver.

IV. Examples

The following examples describe selected aspects and embodiments of the present teachings, including exemplary bone plates and exemplary configurations for assembly of bone plates from plate components. These examples and the various features and aspects thereof are included for illustration and are not intended to define or limit the entire scope of the present teachings.

Example 1

Bone Plates with a Multi-Aperture Spanning Portion

This example describes exemplary bone plates having a spanning portion with a plurality of apertures. The apertures may be arranged so that a clip component can be assembled with and secured to a spanning portion at two or more positions along the spanning portion.

FIG. 14 shows an exemplary bone plate 210 for fixing a fractured rib bone. The bone plate may include a spanning component 212 having a spanning portion 214 and a first clip portion 216 formed unitarily. The bone plate also may include one or more additional clip portions, such as clip components 218, 220 formed as separate components.

Spanning portion 214 may include a plurality of spanning apertures 222 arrayed along the length of this portion. Spanning apertures 222, and particularly subsets of these apertures, may be configured to be aligned with one or more clip apertures 224 of each clip portion. In the present illustration, adjacent pairs of the spanning apertures may be aligned with and abutted to adjacent pairs of clip apertures, shown at 226. Accordingly, each clip portion may be disposed at a plurality of selected positions along the spanning portion.

The apertures of the spanning portion may have any suitable spacing. The apertures may have an equal spacing, as shown here, or may have an unequal spacing. For example, the apertures may be configured as groups (such as pairs, triplets, etc.) with unequal spacing between the groups, so that a clip component, with a corresponding number of apertures as each group, may be secured in alignment with a selected group. Alternatively, an unequal spacing may be suitable if each clip portion uses only one aperture assembly with the spanning portion.

In use, spanning component 212 may be positioned on a fractured rib, and one or more clip components 218, 220 may be positioned in alignment with apertures of the spanning portion. For example, the clip components may be positioned so that pairs of clip portions flank fractured regions of the rib. Accordingly, more severely fractured ribs may use a greater number of clip components in combination with the spanning component. In some examples, the spanning portion may be cut to a suitable length according to the length of bone or bone region to be spanned by the bone plate. Accordingly, a greater or lesser length of the spanning portion (or none) may be removed based on a lesser or greater number, respectively, of clip components to be used and/or a shorter or longer region, respectively, of bone to be fixed. Spanning portion 214 may be cut before or after spanning component 212 is positioned on and/or secured to bone.

Alternative configurations may be suitable. In some embodiments, the spanning component may be selected from a set of spanning components with different lengths of spanning portions and/or different numbers/spacings of apertures. In some embodiments, the spanning portion may be formed of a selectable number of modules, to adjust the length of the spanning portion, and/or the spanning portion may be a separate module (or a set of separate modules of various lengths) that can be selected for assembly with clip components.

Example 2

Bone Plates with Arrays of Plate Components

This example describes bone plates that may be assembled as arrays of plate components.

FIG. 15 shows a bone plate 240 including a tandem array of spanning components 242, 244 that overlap and can be secured to one another with fasteners received in aligned apertures, shown at 246. Each spanning component may include a clip portion and a spanning portion. Any suitable number of spanning components, of similar or distinct configuration, may be arrayed. One or more clip components may be secured to a spanning component, or the bone plate may lack a distinct clip component.

Example 3

Bone Plates of Unitary Construction

This example describes exemplary bone plates having a unitary construction.

FIG. 16 shows an exemplary bone plate 260 for fixing a fractured rib. Bone plate 260 may be formed as one component, so that a spanning portion 262 is joined to, and flanked by, clip portions 264, 266.

Example 4

Selected Embodiments

This section describes selected embodiments of the present teachings, presented as a series of indexed paragraphs.

1. A bone plate for fixing a fracture of a bone, comprising (1) first and second bone-facing surfaces configured to face at least substantially opposite surfaces of a fractured bone, each bone-facing surface defining at least one aperture configured to accept a fastener for attaching the bone plate to the fractured bone; and (2) a third bone-facing surface connecting the first and second surfaces and having width approximating a width of the fractured bone.

2. The bone plate of paragraph 1, wherein the first and second surfaces are substantially parallel.

3. The bone plate of paragraph 1, wherein the third surface conforms at least partially to a surface of the fractured bone.

4. The bone plate of paragraph 3, the bone plate being configured to fix a rib bone, wherein the third surface conforms at least partially to a superior surface of the rib bone.

5. The bone plate of paragraph 3, the bone plate being configured to fix a clavicle bone, wherein the third surface conforms at least partially to a superior surface of the clavicle bone.

6. The bone plate of paragraph 1, wherein at least one of the apertures is configured to engage a threaded fastener.

7. The bone plate of paragraph 1, wherein the apertures define at least one aligned pair of apertures configured to accept a threaded fastener.

8. The bone plate of paragraph 1, wherein the bone plate includes a first anchor portion in which the first and second surfaces are overlapping, a spanning portion in which a longer one of the first and second surfaces is configured to span a fracture, and a second anchor portion including a detachable anchor clip.

9. The bone plate of paragraph 8, wherein each anchor portion includes at least one pair of aligned apertures configured to accept a fastener for attaching the bone plate to the bone, and wherein at least one aperture of each aligned pair is configured to engage a threaded bone screw.

10. The bone plate of paragraph 9, wherein exactly one aperture of each aligned pair is configured to engage a threaded bone screw, and wherein exactly one aperture of each aligned pair defines an elongate reduction slot.

11. The bone plate of paragraph 8, wherein the anchor clip includes a first engagement portion configured to at least partially overlap and engage with the longer bone-facing surface, a second engagement portion opposing the first engagement portion, and a bridge portion connecting the engagement portions and having a width approximating the width of the fractured bone.

12. The bone plate of paragraph 8, wherein the anchor clip is configured to mount to the spanning portion on an opposite side of the fracture from the first anchor portion.

13. The bone plate of paragraph 8, wherein a portion of the anchor clip is configured to mount alternatively to a bone-facing surface of the spanning portion, such that the anchor clip lies between the spanning portion and the bone, or to a non-bone-facing surface of the spanning portion, such that the spanning portion lies between the anchor clip and the bone.

14. A bone plate for fixing a fracture of a rib, comprising (1) a first bone-facing surface for extending along one surface of the rib; (2) a second bone-facing surface opposing the first bone-facing surface, for extending along another surface of the rib; and (3) a third bone-facing surface connecting the first and second bone-facing surfaces.

15. The bone plate of paragraph 14, wherein the third bone-facing surface is shaped to at least partially conform to a superior surface of the rib.

16. The bone plate of paragraph 14, wherein the first and second bone-facing surfaces each define at least one aperture configured to accept a fastener for attaching the bone plate to the rib.

17. The bone plate of paragraph 16, wherein at least one of the apertures configured to engage a threaded bone screw.

18. The bone plate of paragraph 16, the plate including a first region in which the first and second bone-facing surfaces overlap, and a second region in which the first bone-facing surface is configured to extend beyond the second bone-facing surface along the rib.

19. The bone plate of paragraph 18, further comprising a U-shaped anchor clip attachable to the first bone-facing surface in the second region.

20. The bone plate of 18, wherein the second region is configured to span the fracture.

21. The bone plate of paragraph 18, where the anchor clip defines at least one aperture configured to accept a fastener for attaching the bone plate to the rib.

22. A bone plate for fixing a fracture of a rib, comprising: (1) a first component including first and second opposing bone-facing surfaces connected by a third bone-facing surface, wherein at least one of the opposing surfaces defines a spanning portion configured to span the fracture; and (2) a second component including first and second opposing bone-facing engagement portions connected by a bone-facing bridge portion, wherein at least one of the engagement portions is configured to partially overlap and engage with the first component.

23. The bone plate of paragraph 22, wherein each component defines at least one aligned pair of apertures configured to accept a fastener for attaching the bone plate to the rib.

24. The bone plate of paragraph 23, wherein one aperture of each aligned pair is a reduction slot, and wherein the other aperture of each aligned pair is configured to securely engage a threaded bone screw.

25. The bone plate of paragraph 22, wherein the first and second surfaces of the first component are at least substantially parallel, and wherein the first and second portions of the second component are at least substantially parallel.

26. The bone plate of paragraph 22, wherein the third bone-facing surface of the first component and the bridge portion of the second component each conform at least partially to a superior surface of a rib bone.

27. A method of fixing a fracture of a bone, comprising (1) positioning a first bone plate component with three bone-facing surfaces of the first component disposed substantially adjacent three surfaces of a fractured bone, wherein exactly one of the three bone-facing surfaces spans the fracture; (2) positioning a second bone plate component with two bone-facing surfaces of the second component disposed substantially adjacent two surfaces of the fractured bone and with a third surface of the second component disposed substantially adjacent the exactly one bone-facing surface of the first component that spans the fracture; (3) attaching the second component to the first component; and (4) attaching the first and second components to the bone.

28. The method of paragraph 27, wherein the fractured bone is a rib.

29. The method of paragraph 27, wherein the fractured bone is a clavicle.

30. The method of paragraph 27, wherein the exactly one bone-facing surface of the first component faces an external surface of the fractured bone.

31. The method of paragraph 27, wherein the third surface of the second component is disposed substantially adjacent a surface of the fractured bone.

32. The method of paragraph 27, further comprising measuring the fractured bone to determine appropriate dimensions of the first and second bone plate components.

33. The method of paragraph 32, further comprising bending the first and second bone plate components to fit the fractured bone.

34. The method of paragraph 33, wherein the step of bending the components is performed intraoperatively.

35. A method of fixing a fractured rib, comprising (1) measuring a thickness of the rib; (2) intraoperatively contouring at least a first component of a bone plate to at least substantially match the measured thickness of the rib; (3) positioning the bone plate component on the rib such that at least a portion of the component spans the fracture; and (4) attaching the bone plate component to the rib.

36. The method of paragraph 35, further comprising drilling at least one hole through the rib for attaching the component to the rib.

37. The method of paragraph 36, the step of drilling being performed using a drill bit, further comprising adjusting a depth stop on the drill bit to match the thickness of the rib.

38. The method of paragraph 36, wherein the step of attaching includes aligning at least one aperture in the bone plate with the at least one hole through the rib, and inserting a fastener through the aperture and into the hole.

39. The method of paragraph 36, wherein the step of attaching includes aligning at least two apertures in the bone plate with the at least one hole through the rib, and inserting a threaded bone screw through the at least two apertures and through the hole, at least one of the at least two apertures being configured to securely engage one or more threads of the bone screw.

40. The method of paragraph 35, further comprising (4) contouring a second component of the bone plate to at least substantially match the thickness of the rib; and (5) attaching the second component to at least one of the first component and the rib.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A device for fixing a bone, comprising:
   a bone plate including
      a pair of clip portions each being at least generally U-shaped and configured to wrap partially around a bone to opposing surfaces of the bone, each clip portion including a pair of arms extending from a bridge region that connects the pair of arms, the pair of arms of at least one clip portion defining a pair of aligned apertures, and
      a spanning portion connecting the clip portions and configured to extend along the bone between the pair of clip portions; and
   a fastener configured to extend through the bone and to each of the aligned apertures,
   wherein each bridge region has an at least substantially convex outer surface facing in a respective direction, and wherein the respective directions that the outer surfaces of the bridge regions face are about the same.

2. The device of claim 1, wherein the spanning portion bridges the clip portions by extending at least substantially from only one arm of each clip portion.

3. The device of claim 1, wherein each arm defines a plane, and wherein the spanning portion defines a plane oriented at least generally parallel to the plane defined by an arm of a clip portion.

4. The device of claim 1, wherein each clip portion defines a respective pair of aligned apertures configured to receive a fastener that extends through the bone and to each of the aligned apertures of the respective pair.

5. The device of claim 1, wherein the fastener locks to at least one aperture of the pair of aligned apertures when the fastener is received in each of the aligned apertures and extends through the bone.

6. The device of claim 5, wherein the fastener locks to only one aperture of the pair of aligned apertures.

7. The device of claim 6, wherein the only one aperture that the fastener locks to is elongate.

8. The device of claim 1, wherein the spanning portion is unitary with both of the clip portions.

9. The device of claim 1, wherein the clip portions are formed by discrete components.

10. The device of claim 1, wherein the bone plate is configured to be installed on a rib bone.

11. A device for fixing a bone, comprising:
a bone plate including
a pair of clip portions each being at least generally U-shaped and configured to wrap partially around a bone to opposing surfaces of the bone, each clip portion including a pair of arms extending from a bridge region that connects the pair of arms, the pair of arms of at least one clip portion defining a pair of aligned apertures, and
a spanning portion connecting the clip portions and configured to extend along the bone between the pair of clip portions; and
a fastener configured to extend through the bone and to each of the aligned apertures,
wherein each arm defines a plane, and wherein the spanning portion defines a plane oriented at least generally parallel to the plane defined by an arm of a clip portion.

12. The device of claim 11, wherein the spanning portion bridges the clip portions by extending at least substantially from only one arm of each clip portion.

13. The device of claim 11, wherein each clip portion defines a respective pair of aligned apertures configured to receive a fastener that extends through the bone and to each of the aligned apertures of the respective pair.

14. The device of claim 11, wherein the fastener locks to at least one aperture of the pair of aligned apertures when the fastener is received in each of the aligned apertures and extends through the bone.

15. The device of claim 14, wherein the fastener locks to only one aperture of the pair of aligned apertures.

16. The device of claim 15, wherein the only one aperture that the fastener locks to is elongate.

17. The device of claim 11, wherein the spanning portion is unitary with both of the clip portions.

18. The device of claim 11, wherein the clip portions are formed by discrete components.

19. The device of claim 11, wherein the bone plate is configured to be installed on a rib bone.

20. A device for fixing a bone, comprising:
a bone plate including
a pair of clip portions each being at least generally U-shaped and configured to wrap partially around a bone to opposing surfaces of the bone, each clip portion including a pair of arms extending from a bridge region that connects the pair of arms, the pair of arms of at least one clip portion defining a pair of aligned apertures, and
a spanning portion connecting the clip portions and configured to extend along the bone between the pair of clip portions; and
a fastener configured to extend through the bone and to each of the aligned apertures such that the fastener locks to at least one of the aligned apertures,
wherein each bridge region includes an inner surface and an outer surface that oppose each other, wherein the outer surface of each bridge region faces away from the pair of arms of such bridge region, and wherein the outer surfaces of the bridge regions both face in about a same direction.

21. The device of claim 20, wherein the spanning portion bridges the clip portions by extending at least substantially from only one arm of each clip portion.

22. The device of claim 20, wherein each arm defines a plane, and wherein the spanning portion defines a plane oriented at least generally parallel to the plane defined by an arm of a clip portion.

23. The device of claim 20, wherein each clip portion defines a respective pair of aligned apertures configured to receive a fastener that extends through the bone and to each of the aligned apertures of the respective pair.

24. The device of claim 20, wherein the clip portions are formed by discrete components.

25. The device of claim 20, wherein the bone plate is configured to be installed on a rib bone.

26. A device for fixing a bone, comprising:
a bone plate including
a pair of clip portions each being at least generally U-shaped and configured to wrap partially around a bone to opposing surfaces of the bone, each clip portion including a first arm and a second arm extending from a bridge region that connects the arms, the first and second arm of at least one clip portion defining a pair of aligned apertures, and
a spanning portion connecting the clip portions and configured to extend along the bone between the first arm of each clip portion; and
a fastener configured to extend through the bone and to each of the aligned apertures such that the fastener locks to at least one of the aligned apertures,
wherein the spanning portion and the first arm of a clip portion each include an inner surface and an outer surface that oppose one another, and wherein the outer surface of the first arm of the clip portion and the outer surface of the spanning portion both face in about a same direction.

* * * * *